(12) United States Patent
Siu et al.

(10) Patent No.: US 10,287,328 B2
(45) Date of Patent: May 14, 2019

(54) TREATMENT OF DIABETES, TOLL-LIKE RECEPTOR 4 MODULATORS AND METHODS FOR USING THE SAME

(71) Applicant: KeMyth Biotech Co., Ltd., Hsinchu (TW)

(72) Inventors: Leung-Kei Siu, Taipei (TW); Pele Choi-Sing Chong, Toronto (CA); Feng-Yee Chang, Taipei (TW); Chih-Hsiang Leng, Taipei (TW)

(73) Assignee: KeMyth Biotech Co., Ltd., Taipei (TW)

( * ) Notice: Subject to any disclaimer, the term of this patent is extended or adjusted under 35 U.S.C. 154(b) by 0 days.

(21) Appl. No.: 15/441,390

(22) Filed: Feb. 24, 2017

(65) Prior Publication Data

US 2017/0260241 A1 Sep. 14, 2017

Related U.S. Application Data

(60) Provisional application No. 62/305,164, filed on Mar. 8, 2016.

(51) Int. Cl.
| | |
|---|---|
| C07K 14/315 | (2006.01) |
| A61K 38/00 | (2006.01) |
| A61P 29/00 | (2006.01) |
| A61P 3/10 | (2006.01) |
| C07K 14/705 | (2006.01) |

(52) U.S. Cl.
CPC ........ C07K 14/3156 (2013.01); C07K 14/705 (2013.01); *A61K 38/00* (2013.01)

(58) Field of Classification Search
CPC ... A61K 38/00; C07K 14/705; C07K 14/3156
See application file for complete search history.

(56) References Cited

U.S. PATENT DOCUMENTS

2006/0257421 A1* 11/2006 Ochs .................... A61K 39/092
424/190.1

FOREIGN PATENT DOCUMENTS

CA 2931570 A1 6/2015

OTHER PUBLICATIONS

Savva et al, Targeting Toll-like receptors: promising therapeutic strategies for the management of sepsis-associated pathology and infectious diseases, Front. Immunol., 2013, 18, pp. 1-16.*
Dowling et al, Toll-like receptors: the swiss army knife of immunity and vaccine development, Clinical & Translational Immunology, 2016, 5, pp. 1-10.*
Dasu et al, Increased Toll-Like Receptor (TLR) Activation and TLR Ligands in Recently Diagnosed Type 2 Diabetic Subjects, Diabetes Care, 2010, 33, pp. 861-868.*
Peri et al, Therapeutic targeting of innate immunity with Toll-like receptor 4 (TLR4) antagonists, Biotechnology Advances, 2012, 30, pp. 251-260.*
Yampolsky et al, The Exchangeability of Amino Acids in Proteins, Genetics, 2005, 170, pp. 1459-1472.*
Rudinger, Peptide Hormones, JA Parsons, Ed., 1976, pp. 1-7.* SIGMA, 2004, pp. 1-2.*
Berendsen, A Glimpse of the Holy Grail?, Science, 1998, 282, pp. 642-643.*
Voet et al, Biochemistry, John Wiley & Sons Inc., 1995, pp. 235-241.*
Ngo et al, Computational Complexity, Protein Structure Protection, and the Levinthal Paradox, 1994, pp. 491-494.*
Bradley et al., Limits of Cooperativity in a Structurally Modular Protein: Response of the Notch Ankyrin Domain to Analogous Alanine Substitutions in Each Repeat, J. Mol. BloL (2002) 324, 373-386.*
Lu et al, TLR4 antagonist reduces early-stage atherosclerosis in diabetic apolipoprotein E-deficient mice, Journal of Endocrinology, 2013, 216, pp. 61-71.*
Abe et al, Cbl-b is a Critical Regulator of Macrophage Activation Associated With Obesity-Induced Insulin Resistance in Mice, Diabetes, 2013, 62, pp. 1957-1969.*
Lysakova-Devine et al, Viral Inhibitory Peptide of TLR4, a Peptide Derived from Vaccinia Protein A46, Specifically Inhibits TLR4 by Directly Targeting MyD88 Adaptor-Like and TRIF-Related Adaptor Molecule, The Journal of Immunology, 2010, 185, pp. 4261-4271.*
GenPept Accession No. WP_050295188.1. Aug. 6, 2015, 1 page.
Srivastava et al., The apoptotic response to pneumolysin is Toll-like receptor 4 dependent and protects against pneumococcal disease. Infect Immun. Oct. 2005;73(10):6479-87.
Wang et al., High glucose induces and activates Toll-like receptor 4 in endothelial cells of diabetic retinopathy. Diabetol Metab Syndr. Oct. 13, 2015;7:89. doi: 10.1186/s13098-015-0086-4.

* cited by examiner

*Primary Examiner* — Karlheinz R. Skowronek
*Assistant Examiner* — Li N Komatsu
(74) *Attorney, Agent, or Firm* — Wolf, Greenfield & Sacks, P.C.

(57) ABSTRACT

The present invention relates to treatment of diabetes, toll-like receptor 4 (TLR-4) modulators and methods for using the same. Particularly, the present invention provides an isolated peptide from pneumolysin (PLY peptide) which is effective in treatment of diabetes. In addition, the PLY peptide of the present invention is a TLR-4 antagonist and thus can be used in the treatment of a disease or condition associated with TLR-4 activation. The present invention also provides treatment of diabetes with a TLR-4 antagonist.

19 Claims, 19 Drawing Sheets
Specification includes a Sequence Listing.

PLY4         NGDLLLDHSG AYVAQYYITW NELSYDHQGK EVLTPKAWDR
(SEQ ID NO: 3)   NGQDLTA_HFT TSIPLKGNVR NLSVKIRECT GLAWEWW_RTV
             YEKTDLPLVR KRTISIWGTT LYPQVEDKVE ND

SEQ ID NO: 3 = SEQ ID NO: 11 (underline with double-line) + SEQ ID NO: 12 (underline with single-line)
    SEQ ID NO: 11 (47 aa) comprising SEQ ID NO: 9 (5 aa, QDLTA, bold)
    SEQ ID NO: 12 (65aa) comprising SEQ ID NO: 10 (30 a.a., italics)

C70PLY4      QDLTA_HFTTS IPLKGNVRNL SVKIRECTGL AWEWW_RTVYE
(SEQ ID NO: 4)   KTDLPLVRKR TISIWGTTLY PQVEDKVEND

SEQ ID NO: 4 = SEQ ID NO: 9 (QDLTA, bold) + SEQ ID NO: 12 (underline with single-line)
    SEQ ID NO: 9 (5 aa, QDLTA)
    SEQ ID NO: 12 (65aa) comprising SEQ ID NO: 10 (30 a.a., italics)

N35PLY4      QDLTA_HFTTS IPLKGNVRNL SVKIRECTGL AWEWW_
(SEQ ID NO: 5)

SEQ ID NO: 5 = SEQ ID NO: 9 (QDLTA, bold) + SEQ ID NO: 10 (italics)
    SEQ ID NO: 9 (5 aa, QDLTA)
    SEQ ID NO: 10 (30 a.a., italics)

N35PLY4      QDLTA_HFTTS IPLKGNVRNL SVKIKECTGL AWEWW_
m25K (SEQ ID NO: 6)

SEQ ID NO: 6 = SEQ ID NO: 9 (QDLTA, bold) + SEQ ID NO: 13 (italics)
    SEQ ID NO: 9 (5 aa, QDLTA)
    SEQ ID NO: 13 (30 a.a., italics, SEQ ID NO: 10 with one point mutation)

N35PLY4m     QDLTA_HFTTS IPLKGNVRNL SVKLKECTGL AWEWW_
24L25K (SEQ ID NO: 7)

SEQ ID NO: 7 = SEQ ID NO: 9 (QDLTA, bold) + SEQ ID NO: 14 (italics)
    SEQ ID NO: 9 (5 aa, QDLTA)
    SEQ ID NO: 14 (30 a.a., italics, SEQ ID NO: 10 with two point mutaitons)

M50PLY4          _HFTTS IPLKGNVRNL SVKIRECTGL AWEWW_
(SEQ ID NO: 8)   RTVYEKTDLP LVRKRTISIW

Fig. 2

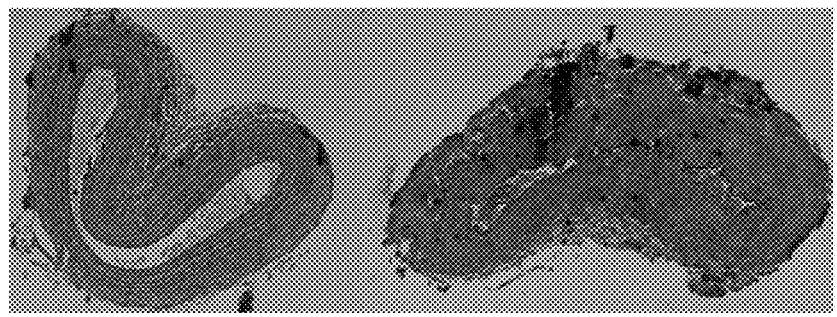
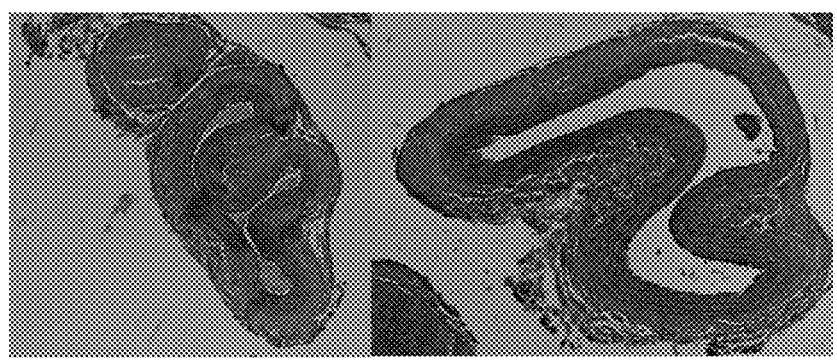
Fig. 8

A.
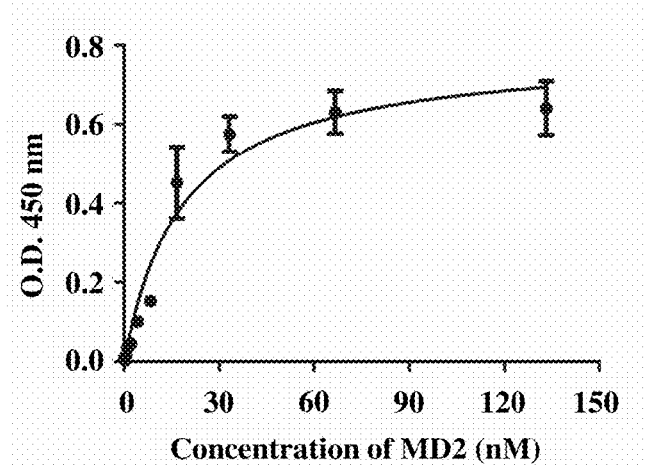
B.
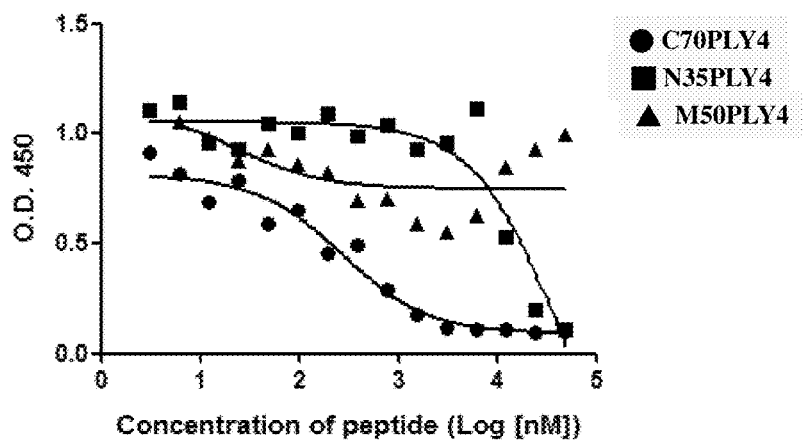
Fig. 13

A.
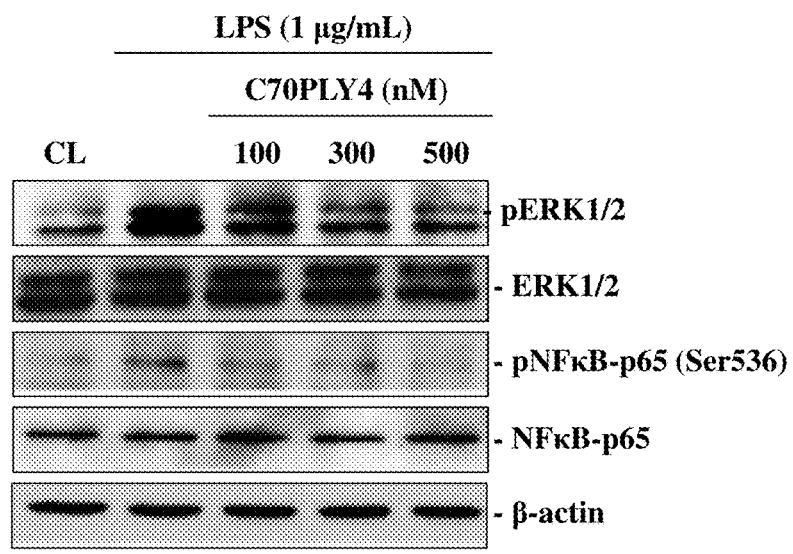
B.
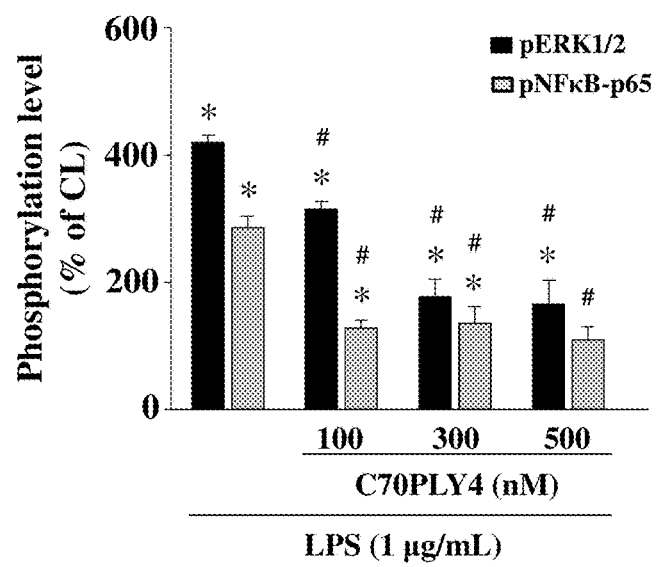
Fig. 14

TREATMENT OF DIABETES, TOLL-LIKE RECEPTOR 4 MODULATORS AND METHODS FOR USING THE SAME

RELATED APPLICATION

This application claims priority to U.S. Provisional Application No. 62/305,164, filed on Mar. 8, 2016, the content of which is hereby incorporated by reference in its entirety.

TECHNOLOGY FIELD

The present invention relates to treatment of diabetes and other diseases/disorders using toll-like receptor 4 (TLR-4) modulators. Particularly, the present invention provides an isolated peptide from pneumolysin (PLY peptide) which is effective in regulating TLR-4 activity and treating diabetes, as well as other diseases or disorders associated with TLR-4 activation.

BACKGROUND OF THE INVENTION

Diabetes is a disorder of sugar metabolism due to deficiency in the production of insulin by the pancreas or ineffectiveness of the insulin produced. The disease causes increased levels of glucose in the blood and results in damages to many of the body's tissues or organs, such as the blood vessels and the nerves.

There are two forms of diabetes, type I diabetes and type II diabetes. Type I diabetes, also called insulin-dependent diabetes mellitus (IDDM), normally develops in children and the patients must administer insulin by injection for their entire life time. Type II diabetes, also called non-insulin-dependent diabetes mellitus (NIDDM), is highly associated with high fat diet and obesity. There are many medications to treat Type 2 diabetes, including drugs that reduce glucose through urination such as INVOKANA® (canagliflozin), a sodium-glucose co-transporter 2 (SGLT2) inhibitor releasing excess glucose in the body through urination; drugs that increase insulin sensitivity such as GLUCOPHAGE® (metformin), ACTOS™ (pioglitazone), and AVANDIA® (rosiglitazone); drugs that stimulate insulin production by the pancreas such as Sulfonylureas and non-sulfonylurea secretagogues; and drugs that slow digestion of carbohydrates such as alpha-glucosidase inhibitors and amylin analogues and dipeptidyl peptidase-4 inhibitors (DPP-4). BYETTA® (Exenatide) is a newly developed injectable drug which is a glucagon-like-peptide-1 (GLP-1) analog and lowers blood sugar by increasing the release of insulin from the pancreas. However, there still have some limitations and possible side effects for these anti-diabetic drugs, such as hypoglycermia, weight gain, cardiovascular problems, nausea and flatulence. As a result, there remains a need for alternative drugs for treatment of diabetes. So far no report discloses use of a TLR-4 antagonist for treatment of diabetes.

TLR-4 is a member of the Toll-like receptor (TLR) family. It is a cell surface, transmembrane receptor which primarily recognizes bacterial lipopolysaccharides and upon activation plays an important role in the induction of inflammatory pathways.

There is increasing evidence that the production and secretion of pro-inflammatory factors in vascular cells play an important role in atherosclerosis. Intercellular adhesion molecule 1 (ICAM-1), vascular adhesion molecule 1 (VCAM-1), and E-selectin are major biomarkers and endothelial cell (EC) adhesion molecules that regulates the binding and extravasation of leukocytes from the bloodstream to sites of inflammation (Sato J et al., PLoS One 9:e107236). When ECs are activated in response to cytokines, the expression of cell adhesion molecules on their surface is increased markedly. The appearance of soluble cell adhesion molecules in the circulation is thought to be the consequence of their release from the surface of activated ECs because of increased expression (Tesfamariam B et al., Vascul Pharmacol 46:229-237). Several reports have demonstrated the importance of soluble forms of adhesion molecules in the microvascular and macrovascular complications that can arise in patients with type 2 diabetes (Herder C et al., PLoS One 6:e19852; Kalofoutis C et al., Exp Clin Cardiol 12:17-28). Some reports have shown that diabetes mellitus (DM) is associated with atherosclerotic and inflammatory disease (Kim J A et al., Circulation 113:1888-1904; Orasanu G et. al., J Am Coll Cardiol 53:S35-42). Among the cardiovascular risk factors documented in diabetes, hyperglycemia appears to be an independent risk factor for diabetic vascular complications (Monnier L et. al., JAMA 295:1681-1687; Wright R J et al., Diabetes Metab Res Rev 24:353-363).

Some reports have shown that loss of TLR4 function partially protects against peripheral and cardiac glucose metabolic derangements during a long-term high-fat diet and a TLR4 antagonist protects against aldosterone-induced cardiac and renal Injury (Jackson E E et al., PLoS One 10:e0142077; Zhang Y et al., PLoS One 10:e0142456). Some reports also have shown that TLR-4 is associated with colorectal cancer progression and metastasis, gastric cancer progression, periodontitis and urinary tract infection (Chen T C et al., Cell Microbiol 13:1703-1713; Chrzeszczyk D et al., Adv Clin Exp Med 24:1059-1070). Lu et al. disclose that Rs-LPS used as a TLR4 antagonist has no effect on glucose and lipid changes induced by high-fat diet, suggesting that Rs-LPS inhibits atherosclerosis in diabetic LDLR−/− mice through mechanisms independent of metabolic control (Lu Z et al., Immunobiology 220 (11): 1246-1254).

Pneumolysin, an intracellular thiol-activated toxin with cytolytic and complement activating properties, is one of the major virulence factor containing in all *Streptococcus. pneumoniae* (Rabes A et al., Curr Top Microbiol Immunol 397:215-227). *S. pneumonia* infections are responsible for the induction of inflammation caused by pneumolysin, which damages the blood vessels in the lungs and causes bleeding into the air spaces. Also, recent study shows that pneumolysin is possibly a chemo-attractant of neutrophils transendothelial migration in pneumonia model (Moreland J G et al., Am J Physiol Lung Cell Mol Physiol 290:L833-840).

BRIEF SUMMARY OF THE INVENTION

The present invention is based on the unexpected finding that a truncated peptide from pneumolysin (PLY) removes the toxicity to cells and exhibits anti-diabetes activities, including lowering blood glucose levels and increasing insulin levels. Therefore, the PLY peptide of the present invention can be used in the treatment of diabetes and its complications. It is further found in the present invention that the truncated PLY peptide acts as a toll-like receptor 4 (TLR-4) antagonist and thus can be used in the treatment of a disease or condition associated with TLR-4 activation such as an inflammatory disorder due to TLR-4 activation e.g. atherosclerosis. The present invention also provides treatment of diabetes with a TLR-4 antagonist.

In some aspect, provided herein is an isolated peptide, comprising: (i) a first segment that comprises the amino acid motif of QDLTA (SEQ ID NO: 9); and (ii) a second segment that comprises an amino acid sequence at least 85% identical to SEQ ID NO: 10. The C-terminus of the first segment is linked to the N-terminus of the second segment. The isolated peptide may have up to 150 amino acids in length.

In some embodiments, the second segment may comprise an amino acid sequence at least 90% identical to SEQ ID NO:10, for example, at least 95% identical to SEQ ID NO:10. In some embodiments, the second segment may include mutations at up to 5 amino acid residues in SEQ ID NO:10. For example, the second segment may include one or more amino acid substitutions at one or more of positions 19 and 20 in SEQ ID NO:10. In some specific examples, the second segment is set forth as SEQ ID NO: 10, 12, 13 or 14.

In some embodiments, the first segment is set forth as SEQ ID NO: 11 or SEQ ID NO:9.

In some embodiments, the isolated peptide described herein comprises an amino acid sequence selected from the group consisting of SEQ ID NOs:3-7.

In another aspect, the present disclosure provides a recombinant nucleic acid comprising a nucleotide sequence encoding any of the peptides as described herein. Such a nucleic acid may be a vector comprising the coding sequence noted herein. In some examples, the vector is an expression vector.

In yet another aspect, provided herein are host cells comprising any of the recombinant nucleic acids described herein.

Any of the peptides or nucleic acids may be formulated to form a composition, for example, a pharmaceutical composition, which further comprises a physiologically acceptable carrier.

Also provided herein is a method for treating diabetes (e.g., type II diabetes) or a complication of diabetes in a subject in need thereof, comprising administering to the subject an effective amount of any of the peptides or any of the nucleic acids encoding such as described herein, or a composition comprising such. In some instances, the effective amount of the peptide or nucleic acid is sufficient to lower blood glucose levels or increase insulin levels of the subject. In some instances, the subject may have one of more complications of diabetes, including diabetic retinopathy, diabetic cataracts, diabetic nephropathy, diabetic neuropathy, diabetic cardiovascular disease (e.g., atherosclerosis) and diabetic skin disease.

Further, provided herein is a method for inhibiting the activity of TLR-4 in a subject, comprising administering to a subject in need thereof an effective amount of a TLR-4 antagonist, e.g., any of the peptides described herein. In some instances, the TLR-4 antagonist blocks the binding of a MD2 protein to TLR-4. In some instances, the TLR-4 antagonist is an anti-TLR-4 antibody. In other instances, the TLR-4 antagonist is an interfering nucleic acid targeting TLR-4, or a small molecule that inhibits TLR-4.

The subject to be treated by the methods described herein may be a human patient having or suspected of having a disease or condition associated with TLR-4 activation. Such a disease or condition may be an inflammatory disorder due to TLR4 activation, particularly atherosclerosis. In some instances, the subject is a diabetic. In other instances, the subject is a non-diabetic. Alternatively or in addition, the subject may be a human patient having or suspected of having diabetes (e.g., type II diabetes) or a complication thereof.

The effective amount of the TLR-4 antagonist is sufficient to lower blood glucose levels or increase insulin levels of the subject.

Also within the scope of the present disclosure are pharmaceutical compositions for use in treating a disease related to TLR-4, the composition comprising any of the peptides described herein or nucleic acids encoding such, and a pharmaceutically acceptable carrier. Such diseases may be type II diabetes, or atherosclerosis. Further, described herein are uses of a peptide described herein or a nucleic acid encoding such for manufacturing a medicament for treating a disease associated with TLR-4.

The details of one or more embodiments of the invention are set forth in the description below. Other features or advantages of the present invention will be apparent from the following detailed description of several embodiments, and also from the appending claims.

BRIEF DESCRIPTION OF THE DRAWINGS

The foregoing summary, as well as the following detailed description of the invention, will be better understood when read in conjunction with the appended drawings. For the purpose of illustrating the invention, there are shown in the drawings embodiments which are presently preferred. It should be understood, however, that the invention is not limited to the precise arrangements and instrumentalities shown.

In the drawings:

FIG. 2 shows the amino acid sequences of PLY4, C70PLY4, N35PLY4, N35PLY4m25K, N35PLY4m24L25K, and M50PLY4.

FIG. 8 shows the attenuated effect of C70PLY4 on the neointima formation and atherosclerotic status induced by STZ in HFD-fed rats.

FIG. 13 includes diagrams showing a high binding affinity ($K_d$ value) of MD2 to TLR4 in the in vitro protein binding assay (panel (A)) and efficient competing with the MD2-binding motif of TLR4 by C70PLY4 (panel (B)).

FIG. 14 includes a photo (panel (A)) showing shows the result of the western blot analysis, indicating the dose-dependent inhibition of C70PLY4 in LPS-induced ERK1/2 and NFκB-p65 subunit activation and a chart (panel (B)) showing the phosphorylation level (percentage of control) based on the results as shown in the top panel, indicating the dose-dependent inhibition of C70PLY4 in LPS-induced ERK1/2 and NFκB-p65 subunit activation.

DETAILED DESCRIPTION OF THE INVENTION

Figure 1:
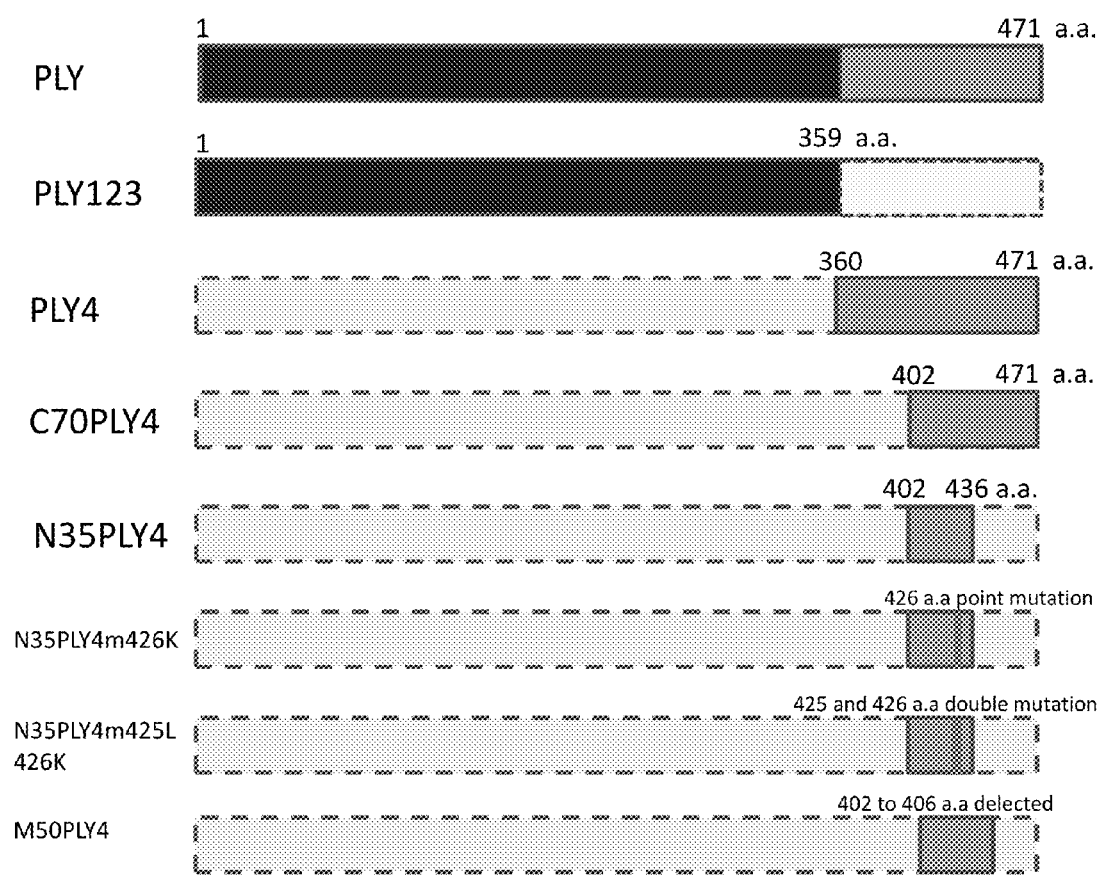
FIG. 1 shows a scheme of (1) a full length pneumococcal pneumolysin (PLY, 1-471 amino acid residues), (2) a fragment of domains 1-3 (PLY123, 1-359 amino acid residues), (3) a fragment of domain 4 (PLY4, 360-471 amino acid residues), (4) a C-terminal 70 amino acid fragment (C70PLY4, 402-471 amino acid residues), (5) a N-terminal 35 amino acid fragment of C70PLY4 (N35PLY4, 402-436 amino acid residues), (6) N35PLY4 with one point mutation at amino acid position 25 with reference to SEQ ID NO: 5 changing from arginine (R) to lysine (K) (N35PLY4m25K), (7) N35PLY4 with double mutations, one at amino acid position 24 with reference to SEQ ID NO: 5 changing from isoleucine (I) to leucine (L) and the other at amino acid position 25 with reference to SEQ ID NO: 5 changing from arginine (R) to lysine (K) (N35PLY4m24L25K) and (8) M50PLY4 (407-456 amino acid residues), a peptide of $6^{th}$ to $55^{th}$ amino acid residues of C70PLY4, lacking the N-terminal motif of QDLTA, (SEQ ID NO: 9).

Unless defined otherwise, all technical and scientific terms used herein have the same meanings as is commonly understood by one of skill in the art to which this invention belongs.

As used herein, the articles "a" and "an" refer to one or more than one (i.e., at least one) of the grammatical object of the article. By way of example, "an element" means one element or more than one element.

The term "comprise" or "comprising" is generally used in the sense of include/including which means permitting the presence of one or more features, ingredients or components. The term "comprise" or "comprising" encompasses the term "consists" or "consisting of."

As used herein, the term "polypeptide" refers to a polymer composed of amino acid residues linked via peptide bonds. The term "peptide" refers to a relatively short polypeptide composed of linked amino acids e.g., 150 amino acids or less e.g. 140 or less, 130 or less, 120 or less, 110 or less, 100 or less, 90 or less, 80 or less, 70 or less, 60 or less, 50 or less or 40 or less amino acids in length.

PLY Peptides and Pharmaceutical Compositions Comprising Such

The PLY peptides described herein refer to non-naturally occurring truncated fragments derived from pneumolysin, or functional variants thereof. Such peptides are different from naturally occurring full-length PLY at least in that such peptides have substantially reduced cell toxicity as compared with their full-length counterpart. Also, PLY peptides show TLR-4 antagonistic activities, which are not observed in the full-length natural counterpart. Accordingly, the PLY peptides are TLR-4 antagonists useful in suppressing the TLR-4 mediated signaling pathway and thus benefit treatment of diseases and disorders associated with abnormal TLR-4 activation.

Bacterial pneumolysin is a 471 amino acid-long polypeptide, which contains four domains. The amino acid sequence of an exemplary pneumolysin is provided in Table 1 below (SEQ ID NO:1). Domains 1-3 ("pneumolysin 123;" SEQ ID NO:2) correspond to amino acid residues 1-359 in SEQ ID NO:1. Domain 4 ("Ply4;" SEQ ID NO:3) corresponds to amino acid residues 360-471 in SEQ ID NO:1.

The PLY peptides described herein may lack Domains 1-3 of a pneumolysin molecule. In some embodiments, a PLY peptide as described herein may comprise an amino acid motif of QDLTA (SEQ ID NO:9), the C-terminus of which is linked to a peptide fragment comprising an amino acid sequence at least 85% (e.g., at least 90%, 95% or 97%) identical to SEQ ID NO: 10. In some instances, any of the PLY peptides may have up to 150 amino acids in length, for example, containing 35-150 amino acid residues, 35-120 amino acid residues, 35-100 amino acid residues, 35-80 amino acid residues, or 35-60 amino acid residues.

To determine the percent identity of two amino acid sequences, the sequences are aligned for optimal comparison purposes (e.g., gaps can be introduced in the sequence of a first amino acid sequence for optimal alignment with a second amino acid sequence). In calculating percent identity, typically exact matches are counted. The determination of percent homology or identity between two sequences can be accomplished using a mathematical algorithm known in the art, such as BLAST and Gapped BLAST programs, the NBLAST and XBLAST programs, or the ALIGN program.

In some embodiments, the PLY peptides described herein may be a fragment of a naturally-occurring pneumolysin, for example, a bacterial pneumolysin. Such a PLY peptides may contain the QDLTA (SEQ ID NO:9) followed by the fragment of SEQ ID NO:10. In addition to the segments of SEQ ID NO:9 and SEQ ID NO:10, a PLY peptide may further contain a segment of the parent pneumolysin that is N-terminal to SEQ ID NO:9, a segment of the parent pneumolysis that is C-terminal to SEQ ID NO:10, or both. The length of a PLY peptide can range from 35-150 amino acids. Exemplary PLY peptides derived from a naturally-occurring pneumolysis include, but are not limited to, PLY4 (SEQ ID NO:3), C70PLY4 (SEQ ID NO:4), and N35PLY4 (SEQ ID NO:5). See Table 1 below.

In other embodiments, the PLY peptides described herein may be a variant of a pneumolysin fragment comprising one or more mutations. It is understandable that a polypeptide may have a limited number of changes or modifications that may be made within a certain portion of the polypeptide irrelevant to its activity or function and still result in a variant with an acceptable level of equivalent or similar biological activity or function. In particular, the PLY peptide of the present invention exhibits the activities to attenuate the TLR-4 activation. Therefore, it is possible to identify the amino acid positions, for example, in the C-terminal sequence of SEQ ID NO: 10 that are essential or non-essential to the activities of the PLY peptide of the present invention to attenuate the TLR-4 activation. Analysis of TLR-4 activation typically is performed by binding of LPS to neutrophils in vivo or by in vitro protein competition binding assay. Binding LPS to neutrophils leads to TLR-4 activation, the level of which can be measured by migration percentages of the neutrophils, for example. A test peptide is determined to be effective in attenuating the TLR-4 activation if the level of the TLR-4 activation decreases in the presence of the test peptide as compared with that in the absence of the test peptide.

In some examples, the PLY peptides may contain mutations (e.g., amino acid residue substitutions) at up to 5 amino acid positions (e.g., 1, 2, 3, 4, or 5) in the region corresponding to SEQ ID NO:10. For example, the PLY peptide may contain a mutation (e.g., amino acid residue substitution) at position 19 and/or position 20 in SEQ ID NO:10 (corresponding to positions 24 and 25 in SEQ ID NO:5, respectively). As shown herein, mutations at these two positions do not affect the TLR-4 inhibitory activity of the PLY peptide. Examples include, but are not limited to, N35PLY4m25K (SEQ ID NO:6) and N35PLY4m24L25K (SEQ ID NO:7).

In some instances, the amino acid residue mutations are conservative amino acid residue substitutions, which, as known in the art, are unlikely to affect the activity of the resultant peptide. As used herein, a "conservative amino acid substitution" refers to an amino acid substitution that does not alter the relative charge or size characteristics of the protein in which the amino acid substitution is made. Variants can be prepared according to methods for altering polypeptide sequence known to one of ordinary skill in the art such as are found in references which compile such methods, e.g. Molecular Cloning: A Laboratory Manual, J. Sambrook, et al., eds., Second Edition, Cold Spring Harbor Laboratory Press, Cold Spring Harbor, N.Y., 1989, or Current Protocols in Molecular Biology, F. M. Ausubel, et al., eds., John Wiley & Sons, Inc., New York. Conservative substitutions of amino acids include substitutions made amongst amino acids within the following groups: (a) M, I, L, V; (b) F, Y, W; (c) K, R, H; (d) A, G; (e) S, T; (f) Q, N; and (g) E, D.

Table 1 shows the amino acid sequences of the full length pneumococcal pneumolysin, its fragments and fragments with mutations in some embodiments of the present invention.

TABLE 1

| Pneumolysin (full length), fragments and fragments with mutation(s) | Amino acid sequence |
|---|---|
| (1) Pneumolysin (471 aa) (SEQ ID NO: 1) | MANKAVNDFI LAMNYDKKKL LTHQGESIEN RFIKEGNQLP DEFVVIERKK RSLSTNTSDI SVTATNDSRL YPGALLVVDE TLLENNPTLL AVDRAPMTYS IDLPGLASSD SFLQVEDPSN SSVRGAVNDL LAKWHQDYGQ VNNVPARMQY EKITAHSMEQ LKVKFGSDFE KTGNSLDIDF NSVHSGEKQI QIVNFKQIYY TVSVDAVKNP GDVFQDTVTV EDLKQRGISA ERPLVYISSV AYGRQVYLKL ETTSKSDEVE AAFEALIKGV KVAPQTEWKQ ILDNTEVKAV ILGGDPSSGA RVVTGKVDMV EDLIQEGSRF TADHPGLPIS YTTSFLRDNV VATFQNSTDY VETKVTAYRN GDLLLDHSGA YVAQYYITWN ELSYDHQGKE VLTPKAWDRN GQDLTAHFTT SIPLKGNVRN LSVKIRECTG LAWEWWRTVY EKTDLPLVRK RTISIWGTTL YPQVEDKVEN D |
| (2) Pneumolysin 123 (domains 1-3; 359 aa) (SEQ ID NO: 2) | MANKAVNDFI LAMNYDKKKL LTHQGESIEN RFIKEGNQLP DEFVVIERKK RSLSTNTSDI SVTATNDSRL YPGALLVVDE TLLENNPTLL AVDRAPMTYS IDLPGLASSD SFLQVEDPSN SSVRGAVNDL LAKWHQDYGQ VNNVPARMQY EKITAHSMEQ LKVKFGSDFE KTGNSLDIDF NSVHSGEKQI QIVNFKQIYY TVSVDAVKNP GDVFQDTVTV EDLKQRGISA ERPLVYISSV AYGRQVYLKL ETTSKSDEVE AAFEALIKGV KVAPQTEWKQ ILDNTEVKAV ILGGDPSSGA RVVTGKVDMV EDLIQEGSRF TADHPGLPIS YTTSFLRDNV VATFQNSTDY VETKVTAYR |
| (3) PLY4 (domain 4; 112 aa) (SEQ ID NO: 3)[1] | NGDLLLDHSG AYVAQYYITW NELSYDHQGK EVLTPKAWDR NGQDLTAHFT TSIPLKGNVR NLSVKIRECT GLAWEWWRTV YEKTDLPLVR KRTISIWGTT LYPQVEDKVE ND SEQ ID NO: 3 = SEQ ID NO: 11 (N-terminal, 11 aa, underline with double-line, comprising QDLTA at its C-terminal) plus SEQ ID NO 12 (C-terminal, 65 aa, underline with single-line, comprising SEQ ID NO: 10, italics, at its N-terminal) |

TABLE 1-continued

| Pneumolysin (full length), fragments and fragments with mutation(s) | Amino acid sequence |
|---|---|
| (4) C70PLY4<br>(402-471 amino acid<br>residues) (SEQ ID NO: 4)[1] | QDLTA_HFTTS IPLKGNVRNL SVKIRECTGL_<br>_AWEWWRTVYE KTDLPLVRKR TISIWGTTLY_<br>PQVEDKVEND<br>SEQ ID NO: 4 = SEQ ID NO: 9 (N-terminal, 5 aa,<br>QDLTA) plus SEQ ID NO 12 (C-terminal, 65 aa,<br>underline with single-line, comprising SEQ ID NO:<br>10, italics, at its N-terminal) |
| (5) N35PLY4<br>(402-436 amino acid<br>residues)<br>(SEQ ID NO: 5)[1] | QDLTA_HFTTS IPLKGNVRNL SVK<u>I</u>RECTGL_<br>_AWEWW_<br>SEQ ID NO: 5 = SEQ ID NO: 9 (N-terminal, 5 aa,<br>QDLTA) plus SEQ ID NO 10 (C-terminal, 30 aa,<br>italics) |
| (6) N35PLY4m25K<br>(402-436 amino acid<br>residues with one mutation at<br>amino acid position 25)[1,2]<br>(SEQ ID NO: 6) | QDLTA_HFTTS IPLKGNVRNL SVK<u>K</u>ECTGL_<br>_AWEWW_<br>SEQ ID NO: 6 = SEQ ID NO: 9 (N-terminal, 5 aa,<br>QDLTA) plus SEQ ID NO 13 (C-terminal, 30 aa,<br>italics, SEQ ID NO: 10 with one point mutation) |
| (7) N35PLY4m24L25K<br>(402-436 amino acid residues<br>with two mutation at amino<br>acid positions 24 and 25)[1,3]<br>(SEQ ID NO: 7) | QDLTA_HFTTS IPLKGNVRNL SVK<u>LK</u> ECTGL_<br>_AWEWW_<br>SEQ ID NO: 7 = SEQ ID NO: 9 (N-terminal, 5 aa,<br>QDLTA) plus SEQ ID NO 14 (C-terminal, 30 aa,<br>italics, SEQ ID NO: 10 with two point mutations) |
| (8) M50PLY4<br>(407-456 amino acid<br>residues)[4]<br>(SEQ ID NO: 8) | _HFTTS IPLKGNVRNL SVKIRECTGL_<br>_AWEWWRTVYE KTDLPLVRKR TISIW_ |

[1]PLY4, C70PLY4, N35PLY4, N35PLY4m25K and N35PLY4m24L25K comprise
(i) a N-terminal motif of QDLTA (SEQ ID NO: 9, five amino acid residues in length, bold) and (ii) a C-terminal sequence of SEQ ID NO: 10 (30 amino acid residues in length, italics)
[2]The amino acid position 25 with reference to SEQ ID NO: 5 corresponds to the amino acid position 426 with reference to SEQ ID NO: 1 (the full length of pneumolysin).
[3]The amino acid positions 24 and 25 with reference to SEQ ID NO: 5 correspond to the amino acid positions 425 and 426 with reference to SEQ ID NO: 1 (the full length of pneumolysin).
[4]M50PLY4 is a peptide of 6th to 55th amino acid residues of C70PLY4, lacking the N-terminal motif of QDLTA (SEQ ID NO: 9).

The PLY peptide of the present invention may be produced by chemical synthesis using techniques well known in the chemistry of proteins such as solid phase synthesis or synthesis in homogenous solution.

Alternatively, the PLY peptide of the present invention may be prepared using recombinant techniques. In this regard, a recombinant nucleic acid comprising a nucleotide sequence encoding a peptide of the present invention and host cells comprising such recombinant nucleic acid are provided. The host cells may be cultured under suitable conditions for expression of the polypeptide of interest. Expression of the polypeptides may be constitutive such that they are continually produced or inducible, requiring a stimulus to initiate expression. In the case of inducible expression, protein production can be initiated when desired by, for example, addition of an inducer substance to the culture medium, for example, isopropyl β-D-1-thiogalactopyranoside (IPTG) or methanol. Polypeptide can be recovered and purified from host cells by a number of techniques known in the art, for example, chromatography e.g., HPLC or affinity columns.

The term "polynucleotide" or "nucleic acid" refers to a polymer composed of nucleotide units. Polynucleotides include naturally occurring nucleic acids, such as deoxyribonucleic acid ("DNA") and ribonucleic acid ("RNA") as well as nucleic acid analogs including those which have non-naturally occurring nucleotides. Polynucleotides can be synthesized, for example, using an automated DNA synthesizer. The term "nucleic acid" typically refers to large polynucleotides. It will be understood that when a nucleotide sequence is represented by a DNA sequence (i.e., A, T, G, C), this also includes an RNA sequence (i.e., A, U, G, C) in which "U" replaces "T." The term "cDNA" refers to a DNA that is complementary or identical to an mRNA, in either single stranded or double stranded form.

The term "complementary" refers to the topological compatibility or matching together of interacting surfaces of two polynucleotides. Thus, the two molecules can be described as complementary, and furthermore the contact surface characteristics are complementary to each other. A first polynucleotide is complementary to a second polynucleotide if the nucleotide sequence of the first polynucleotide is identical to the nucleotide sequence of the polynucleotide binding partner of the second polynucleotide. Thus, the polynucleotide whose sequence 5'-TATAC-3' is complementary to a polynucleotide whose sequence is 5'-GTATA-3'."

The term "encoding" refers to the inherent property of specific sequences of nucleotides in a polynucleotide (e.g., a gene, a cDNA, or an mRNA) to serve as templates for synthesis of other polymers and macromolecules in biological processes having either a defined sequence of nucleotides (i.e., rRNA, tRNA and mRNA) or a defined sequence of amino acids and the biological properties resulting therefrom. Therefore, a gene encodes a protein if transcription and translation of mRNA produced by that gene produces the protein in a cell or other biological system. It is understood by a skilled person that numerous different polynucleotides and nucleic acids can encode the same polypeptide as a result of the degeneracy of the genetic code. It is also understood that skilled persons may, using routine techniques, make nucleotide substitutions that do not affect the polypeptide sequence encoded by the polynucleotides described there to reflect the codon usage of any particular host organism in which the polypeptides are to be expressed. Therefore, unless otherwise specified, a "nucleotide sequence encoding an amino acid sequence" includes all nucleotide sequences that are degenerate versions of each other and that encode the same amino acid sequence. Nucleotide sequences that encode proteins and RNA may include introns.

The term "recombinant nucleic acid" refers to a polynucleotide or nucleic acid having sequences that are not naturally joined together. A recombinant nucleic acid may be present in the form of a vector. "Vectors" may contain a given nucleotide sequence of interest and a regulatory sequence. Vectors may be used for expressing the given nucleotide sequence (expression vector) or maintaining the given nucleotide sequence for replicating it, manipulating it or transferring it between different locations (e.g., between different organisms). Vectors can be introduced into a suitable host cell for the above mentioned purposes. A "recombinant cell" refers to a host cell that has had introduced into it a recombinant nucleic acid.

Examples of vectors include, but are not limited to, plasmids, cosmids, phages, YACs or PACs. Typically, in vectors, the given nucleotide sequence is operatively linked to the regulatory sequence such that when the vectors are introduced into a host cell, the given nucleotide sequence can be expressed in the host cell under the control of the regulatory sequence. The regulatory sequence may comprises, for example and without limitation, a promoter sequence (e.g., the cytomegalovirus (CMV) promoter, simian virus 40 (SV40) early promoter, T7 promoter, and alcohol oxidase gene (AOX1) promoter), a start codon, a replication origin, enhancers, an operator sequence, a secretion signal sequence (e.g., α-mating factor signal) and other control sequence (e.g., Shine-Dalgarno sequences and termination sequences). Preferably, vectors may further contain a marker sequence (e.g., an antibiotic resistant marker sequence) for the subsequent screening procedure. For purpose of protein production, in vectors, the given nucleotide sequence of interest may be connected to another nucleotide sequence other than the above-mentioned regulatory sequence such that a fused polypeptide is produced and beneficial to the subsequent purification procedure. Said fused polypeptide includes, but is not limited to, a His-tag fused polypeptide and a GST fused polypeptide. Therefore, in some embodiments, the peptide of the invention as described herein can be a fused polypeptide with a tag for purification.

In some embodiments, the peptide of the present invention can be said to be "isolated" or "purified" if it is substantially free of cellular material or chemical precursors or other chemicals that may be involved in the process of peptide preparation. It is understood that the term "isolated" or "purified" does not necessarily reflect the extent to which the peptide has been "absolutely" isolated or purified e.g. by removing all other substances (e.g., impurities or cellular components). In some cases, for example, an isolated or purified peptide includes a preparation containing the peptide having less than 50%, 40%, 30%, 20% or 10% (by weight) of other proteins (e.g. cellular proteins), having less than 50%, 40%, 30%, 20% or 10% (by volume) of culture medium, or having less than 50%, 40%, 30%, 20% or 10% (by weight) of chemical precursors or other chemicals involved in synthesis procedures. The term "isolated" or "purified" can also apply in the nucleic acid of the present invention.

According to the present invention, an effective amount of the active ingredient (PLY peptide) may be formulated with a physiologically acceptable carrier into a composition of an appropriate form for the purpose of delivery and absorption. The composition of the present invention particularly comprises about 0.1% by weight to about 100% by weight of the active ingredient, wherein the percentage by weight is calculated based on the weight of the whole composition. In some embodiments, the composition of the present invention can be a pharmaceutical composition or medicament for treatment. In some embodiments, the composition of the present invention can be a food product or supplement.

As used herein, "physiologically acceptable" means that the carrier is compatible with the active ingredient in the composition, and preferably can stabilize said active ingredient and is safe to the receiving individual. Said carrier may be a diluent, vehicle, excipient, or matrix to the active ingredient. Some examples of appropriate excipients include lactose, dextrose, sucrose, sorbose, mannose, starch, Arabic gum, calcium phosphate, alginates, tragacanth gum, gelatin, calcium silicate, microcrystalline cellulose, polyvinyl pyrrolidone, cellulose, sterilized water, syrup, and methylcellulose. The composition may additionally comprise lubricants, such as talc, magnesium stearate, and mineral oil; wetting agents; emulsifying and suspending agents; preservatives, such as methyl and propyl hydroxybenzoates; sweeteners; and flavoring agents. The composition of the present invention can provide the effect of rapid, continued, or delayed release of the active ingredient after administration to the patient.

According to the present invention, the form of the composition may be tablets, pills, powder, lozenges, packets, troches, elixers, suspensions, lotions, solutions, syrups, soft and hard gelatin capsules, suppositories, sterilized injection fluid, and packaged powder.

The composition of the present invention may be delivered via any physiologically acceptable route, such as oral, parenteral (such as intramuscular, intravenous, subcutaneous, and intraperitoneal), transdermal, suppository, and intranasal methods. Regarding parenteral administration, it is preferably used in the form of a sterile water solution, which may comprise other substances, such as salts or glucose sufficient to make the solution isotonic to blood. The water solution may be appropriately buffered (e.g. with a pH value of 3 to 9) as needed. Preparation of an appropriate parenteral composition under sterile conditions may be accomplished with standard pharmacological techniques well known to persons skilled in the art.

Therapeutic Uses of PLY Peptides for Treating TLR-4-Associated Diseases

TLR-4 is a toll-like receptor responsible for activating the innate immune system. TLR-4 can recognize and be activated by lipopolysaccharide (LPS), which is a common component present in bacteria pathogens. Other molecules, such as viral proteins and polysaccharide, are also found as ligands to TLR-4. Unexpectedly, it was found that the PLY peptides described herein are capable of inhibiting TLR-4 activation. Thus, any of the PLY peptides described herein, which possess inhibitory activity against TLR-4, may be used for inhibiting TLR-4 activity in a subject in need of such treatment, thereby benefiting treatment of a disease or disorder associated with abnormal activation of TLR-4.

To practice the method disclosed herein, an effective amount of a composition such as a pharmaceutical composition described herein, comprising one or more of the PLY4 peptides described herein, can be administered to a subject (e.g., a human) in need of the treatment via a suitable route, such as intravenous administration, e.g., as a bolus or by continuous infusion over a period of time, by intramuscular, intraperitoneal, intracerebrospinal, subcutaneous, intra-articular, intrasynovial, intrathecal, oral, inhalation or topical routes. Commercially available nebulizers for liquid formulations, including jet nebulizers and ultrasonic nebulizers are useful for administration. Liquid formulations can be directly nebulized and lyophilized powder can be nebulized after reconstitution. Alternatively, a composition comprising the PLY4 peptide as described herein can be aerosolized using a fluorocarbon formulation and a metered dose inhaler, or inhaled as a lyophilized and milled powder.

The term "effective amount" used herein refers to the amount of an active ingredient to confer a desired biological effect in a treated subject or cell. The effective amount may change depending on various reasons, such as administration route and frequency, body weight and species of the individual receiving said pharmaceutical, and purpose of administration. Persons skilled in the art may determine the dosage in each case based on the disclosure herein, established methods, and their own experience.

The subject to be treated by the methods described herein can be a mammal, more preferably a human. Mammals include, but are not limited to, farm animals, sport animals, pets, primates, horses, dogs, cats, mice and rats. A human subject who needs the treatment may be a human patient having, at risk for, or suspected of having a target disease/disorder, such as diabetes, a complication thereof, or atherosclerosis. A subject having a target disease or disorder can be identified by routine medical examination, e.g., laboratory tests, organ functional tests, CT scans, or ultrasounds. A subject suspected of having any of such target disease/disorder might show one or more symptoms of the disease/disorder. A subject at risk for the disease/disorder can be a subject having one or more of the risk factors for that disease/disorder.

Abnormal TLR-4 activation is associated with various diseases and disorders. It is first disclosed in the present invention that TLR-4 signaling is involved in diabetes development and progression and therefore diabetes can be treated by inhibiting TLR-4 activation. Therefore, in one example, the target disease to be treated by inhibiting TLR-4 activation is diabetes or a complication thereof. Examples of the complication of diabetes includes diabetic retinopathy, diabetic cataracts, diabetic nephropathy, diabetic neuropathy, diabetic cardiovascular disease and diabetic skin disease, but is not limited thereto, as long as it can be caused by diabetes. For treating diabetes or a complication thereof, the PLY peptide may be given to a subject in need of the treatment in an amount effective in lowering blood glucose levels and/or increasing insulin levels in the subject.

In particular embodiments, the disease or condition associated with TLR-4 activation is an inflammatory disorder due to TLR4 activation. In a certain example, the disease or condition associated with TLR-4 activation is atherosclerosis. In particular examples, the subject is diabetic or non-diabetic.

Other diseases/disorders associated with abnormal TLR-4 activation include, but are not limited to, atherosclerosis, cardiovascular diseases, retinopathy, renal hypertrophy and dysfunction, colorectal cancer progression and metastasis, gastric cancer progression, atherosclerosis, periodontitis, urinary tract infection and other inflammatory diseases.

In some embodiments, the individual or subject can be a mammal afflicted with or at risk of atherosclerosis e.g. those who are overweight or obese, have high blood pressure or high blood cholesterol, consume a high fat diet, have a family history of heart disease, suffer from diabetes or smoke.

The term "treating" as used herein refers to the application or administration of a composition including one or more active agents to a subject afflicted with a disorder (e.g. diabetes, atherosclerosis and other inflammatory diseases), a symptom or conditions of the disorder, or a progression or predisposition of the disorder, with the purpose to cure, heal, alleviate, relieve, alter, remedy, ameliorate, improve, or affect the disorder, the symptoms or conditions of the disorder, the disabilities induced by the disorder, or the progression or predisposition of the disorder. Therefore, the term "treating" can also include, depending on the condition of the subject to be treated, preventing the disorder, including preventing onset of the disorder or of any symptoms associated therewith as well as reducing or alleviating the severity of the disorder or any of its symptoms prior to onset.

Treatment of Diabetes with TLR-4 Antagonists

The present disclosure is based, at least in part, on the discovery that the TLR-4 signaling is involved in diabetes development and progression. Accordingly, also provided herein are methods for treating diabetes and/or alleviating at least one symptom thereof with a TLR-4 antagonist via, e.g., inhibition of the TLR-4 pathway, thereby lowering blood glucose levels and/or increase insulin levels. The methods described herein would induce no certain side effects, such as weight gain and cardiovascular problems, As used herein, the term "TLR-4 antagonist" refers to a substance or an agent which can substantially reduce, inhibit, block and/or mitigate activation of TLR-4, including but not limited to, activation of neutrophils, production of pro-inflammatory substances (such as ICAM-1, VCAM-1 and E-selectin) and neutrophil transendothelial migration. TLR4 is a well-characterized cell surface receptor. TLR4 is an atypical member of the LRR (leucine-rich repeats) family and is composed of N-terminal, central, and C-terminal domains. The β sheet of the central domain shows unusually small radii and large twist angles. MD-2, an extracellular protein, binds to the concave surface of the N-terminal and central domains, forming a TLR-4/MD2 dimer for LPS recognition (Ohto U et al., Science (2007) 316:1632-4; KIM H M et al., Cell (2007) 130:906; Park B S et al., Nat (2009) 458:1191). In some embodiments, the TLR-4 antagonists as used herein are capable of inhibiting the interaction between a MD2 protein to TLR-4, for example, by competing the binding site of MD2 in TLR4, thus substantially reducing, inhibiting, blocking and/or mitigating activation of TLR-4.

In addition to the PLY peptides described herein, TLR-4 antagonists for use in the diabetes treatment methods described herein may include an anti-TLR-4 antibody, an antisense nucleic acid molecule directed to a TLR-4 gene, a small interfering RNA (siRNA) directed toward a TLR-4 nucleic acid, or a small molecule TLR-4 inhibitory compound.

An antibody (interchangeably used in plural form) is an immunoglobulin molecule capable of specific binding to a target, such as a carbohydrate, polynucleotide, lipid, polypeptide, etc., through at least one antigen recognition site, located in the variable region of the immunoglobulin molecule. As used herein, the term "antibody" encompasses not only intact (i.e., full-length) polyclonal or monoclonal antibodies, but also antigen-binding fragments thereof (such as Fab, Fab', F(ab')$_2$, Fv), single chain (scFv), mutants thereof, fusion proteins comprising an antibody portion, humanized antibodies, chimeric antibodies, diabodies, linear antibodies, single chain antibodies, multispecific antibodies (e.g., bispecific antibodies) and any other modified configuration of the immunoglobulin molecule that comprises an antigen recognition site of the required specificity, including glycosylation variants of antibodies, amino acid sequence variants of antibodies, and covalently modified antibodies. An antibody includes an antibody of any class, such as IgD, IgE, IgG, IgA, or IgM (or sub-class thereof), and the antibody need not be of any particular class. Depending on the antibody amino acid sequence of the constant domain of its heavy chains, immunoglobulins can be assigned to different classes. There are five major classes of immunoglobulins: IgA, IgD, IgE, IgG, and IgM, and several of these may be further divided into subclasses (isotypes), e.g., IgG1, IgG2, IgG3, IgG4, IgA1 and IgA2. The heavy-chain constant domains that correspond to the different classes of immunoglobulins are called alpha, delta, epsilon, gamma, and mu, respectively. The subunit structures and three-dimensional configurations of different classes of immunoglobulins are well known.

The antibodies to be used in the methods described herein can be murine, rat, human, or any other origin (including chimeric or humanized antibodies). In some examples, the antibody comprises a modified constant region, such as a constant region that is immunologically inert, e.g., does not trigger complement mediated lysis, or does not stimulate antibody-dependent cell mediated cytotoxicity (ADCC). ADCC activity can be assessed using methods disclosed in U.S. Pat. No. 5,500,362. In other embodiments, the constant region is modified as described in Eur. J. Immunol. (1999) 29:2613-2624; PCT Application No. PCT/GB99/01441; and/or UK Patent Application No. 9809951.8.

Any of the antibodies described herein can be either monoclonal or polyclonal. A "monoclonal antibody" refers to a homogenous antibody population and a "polyclonal antibody" refers to a heterogenous antibody population. These two terms do not limit the source of an antibody or the manner in which it is made.

In one example, the antibody used in the methods described herein is a humanized antibody. Humanized antibodies refer to forms of non-human (e.g. murine) antibodies that are specific chimeric immunoglobulins, immunoglobulin chains, or antigen-binding fragments thereof that contain minimal sequence derived from non-human immunoglobulin. For the most part, humanized antibodies are human immunoglobulins (recipient antibody) in which residues from a complementary determining region (CDR) of the recipient are replaced by residues from a CDR of a non-human species (donor antibody) such as mouse, rat, or rabbit having the desired specificity, affinity, and capacity. In some instances, Fv framework region (FR) residues of the human immunoglobulin are replaced by corresponding non-human residues. Furthermore, the humanized antibody may comprise residues that are found neither in the recipient antibody nor in the imported CDR or framework sequences, but are included to further refine and optimize antibody performance. In general, the humanized antibody will comprise substantially all of at least one, and typically two, variable domains, in which all or substantially all of the CDR regions correspond to those of a non-human immunoglobulin and all or substantially all of the FR regions are those of a human immunoglobulin consensus sequence. The humanized antibody optimally also will comprise at least a portion of an immunoglobulin constant region or domain (Fc), typically that of a human immunoglobulin. Antibodies may have Fc regions modified as described in WO 99/58572. Other forms of humanized antibodies have one or more CDRs (one, two, three, four, five, six) which are altered with respect to the original antibody, which are also termed one or more CDRs "derived from" one or more CDRs from the original antibody. Humanized antibodies may also involve affinity maturation.

In another example, the antibody described herein is a chimeric antibody, which can include a heavy constant region and a light constant region from a human antibody. Chimeric antibodies refer to antibodies having a variable region or part of variable region from a first species and a constant region from a second species. Typically, in these chimeric antibodies, the variable region of both light and heavy chains mimics the variable regions of antibodies derived from one species of mammals (e.g., a non-human mammal such as mouse, rabbit, and rat), while the constant portions are homologous to the sequences in antibodies derived from another mammal such as human. In some embodiments, amino acid modifications can be made in the variable region and/or the constant region.

In some examples, the antibody disclosed herein specifically binds a target antigen, such as human TLR-4. An antibody that "specifically binds" (used interchangeably herein) to a target or an epitope is a term well understood in the art, and methods to determine such specific binding are also well known in the art. A molecule is said to exhibit "specific binding" if it reacts or associates more frequently, more rapidly, with greater duration and/or with greater affinity with a particular target antigen than it does with alternative targets. An antibody "specifically binds" to a target antigen if it binds with greater affinity, avidity, more readily, and/or with greater duration than it binds to other substances. For example, an antibody that specifically (or preferentially) binds to a TLR-4 epitope is an antibody that binds this TLR-4 epitope with greater affinity, avidity, more readily, and/or with greater duration than it binds to other TLR-4 epitopes or non-TLR-4 epitopes. It is also understood by reading this definition that, for example, an antibody that specifically binds to a first target antigen may or may not specifically or preferentially bind to a second target antigen. As such, "specific binding" or "preferential binding" does not necessarily require (although it can include) exclusive binding. Generally, but not necessarily, reference to binding means preferential binding.

An anti-TLR-4 antibody is an antibody capable of binding to TLR-4 and inhibits TLR-4 biological activity and/or downstream pathway(s) mediated by TLR-4 signaling. In some examples, an anti-TLR-4 antibody used in the methods described herein suppresses the TLR-4 signaling pathway by at least 20%, at least 40%, at least 50%, at least 75%, at least 90%, at least 100%, or by at least 2-fold, at least 5-fold, at least 10-fold, at least 20-fold, at least 50-fold, at least 100-fold, or at least 1000-fold.

The binding affinity of an anti-TLR-4 antibody to TLR-4 (such as human TLR-4) can be less than any of about 100 nM, about 50 nM, about 10 nM, about 1 nM, about 500 pM, about 100 pM, or about 50 pM to any of about 2 pM. Binding affinity can be expressed $K_D$ or dissociation constant, and an increased binding affinity corresponds to a decreased $K_D$. One way of determining binding affinity of antibodies to TLR-4 is by measuring binding affinity of monofunctional Fab fragments of the antibody. To obtain monofunctional Fab fragments, an antibody (for example, IgG) can be cleaved with papain or expressed recombinantly. The affinity of an anti-TLR-4 Fab fragment of an antibody can be determined by surface plasmon resonance (BIAcore3000™ surface plasmon resonance (SPR) system, BIAcore, INC, Piscaway N.J.). Kinetic association rates ($k_{on}$) and dissociation rates ($k_{off}$) (generally measured at 25° C.) are obtained; and equilibrium dissociation constant ($K_D$) values are calculated as $k_{off}/k_{on}$.

In some embodiments, the antibody binds human TLR-4 and does not significantly bind a TLR-4 from another mammalian species. In some embodiments, the antibody binds human TLR-4 as well as one or more TLR-4 from another mammalian species.

Antibodies capable of interfering with the TLR-4 signaling pathway as described herein can be made by any method known in the art. See, for example, Harlow and Lane, (1988) Antibodies: A Laboratory Manual, Cold Spring Harbor Laboratory, N.Y.

In some embodiments, antibodies specific to the target antigen (e.g., human TLR-4) can be made by the conventional hybridoma technology. The full-length target antigen or a fragment thereof, optionally coupled to a carrier protein such as KLH, can be used to immunize a host animal for generating antibodies binding to that antigen. The route and schedule of immunization of the host animal are generally in keeping with established and conventional techniques for antibody stimulation and production, as further described herein. General techniques for production of mouse, humanized, and human antibodies are known in the art and are described herein. It is contemplated that any mammalian subject including humans or antibody producing cells therefrom can be manipulated to serve as the basis for production of mammalian, including human hybridoma cell lines. Typically, the host animal is inoculated intraperitoneally, intramuscularly, orally, subcutaneously, intraplantar, and/or intradermally with an amount of immunogen, including as described herein.

Hybridomas can be prepared from the lymphocytes and immortalized myeloma cells using the general somatic cell hybridization technique of Kohler, B. and Milstein, C. (1975) Nature 256:495-497 or as modified by Buck, D. W., et al., In Vitro, 18:377-381 (1982). Available myeloma lines, including but not limited to X63-Ag8.653 and those from the Salk Institute, Cell Distribution Center, San Diego, Calif., USA, may be used in the hybridization. Generally, the technique involves fusing myeloma cells and lymphoid cells using a fusogen such as polyethylene glycol, or by electrical means well known to those skilled in the art. After the fusion, the cells are separated from the fusion medium and grown in a selective growth medium, such as hypoxanthine-aminopterin-thymidine (HAT) medium, to eliminate unhybridized parent cells. Any of the media described herein, supplemented with or without serum, can be used for culturing hybridomas that secrete monoclonal antibodies. As another alternative to the cell fusion technique, EBV immortalized B cells may be used to produce the anti-TLR-4 monoclonal antibodies of the subject invention. The hybridomas are expanded and subcloned, if desired, and supernatants are assayed for anti-immunogen activity by conventional immunoassay procedures (e.g., radioimmunoassay, enzyme immunoassay, or fluorescence immunoassay).

Hybridomas that may be used as source of antibodies encompass all derivatives, progeny cells of the parent hybridomas that produce monoclonal antibodies capable of interfering with the TLR-4 signaling pathway. Hybridomas that produce such antibodies may be grown in vitro or in vivo using known procedures. The monoclonal antibodies may be isolated from the culture media or body fluids, by conventional immunoglobulin purification procedures such as ammonium sulfate precipitation, gel electrophoresis, dialysis, chromatography, and ultrafiltration, if desired. Undesired activity if present, can be removed, for example, by running the preparation over adsorbents made of the immunogen attached to a solid phase and eluting or releasing the desired antibodies off the immunogen. Immunization of a host animal with a target antigen or a fragment containing the target amino acid sequence conjugated to a protein that is immunogenic in the species to be immunized, e.g., keyhole limpet hemocyanin, serum albumin, bovine thyroglobulin, or soybean trypsin inhibitor using a bifunctional or derivatizing agent, for example maleimidobenzoyl sulfosuccinimide ester (conjugation through cysteine residues), N-hydroxysuccinimide (through lysine residues), glutaraldehyde, succinic anhydride, SOCl, or $R1N=C=NR$, where R and R1 are different alkyl groups, can yield a population of antibodies (e.g., monoclonal antibodies).

If desired, an antibody (monoclonal or polyclonal) of interest (e.g., produced by a hybridoma) may be sequenced and the polynucleotide sequence may then be cloned into a vector for expression or propagation. The sequence encoding the antibody of interest may be maintained in vector in a host cell and the host cell can then be expanded and frozen for future use. In an alternative, the polynucleotide sequence may be used for genetic manipulation to "humanize" the antibody or to improve the affinity (affinity maturation), or other characteristics of the antibody. For example, the constant region may be engineered to more resemble human constant regions to avoid immune response if the antibody is used in clinical trials and treatments in humans. It may be desirable to genetically manipulate the antibody sequence to obtain greater affinity to the target antigen and greater efficacy in inhibiting the signaling pathway mediated by TLR-4. It will be apparent to one of skill in the art that one or more polynucleotide changes can be made to the antibody and still maintain its binding specificity to the target antigen.

In other embodiments, fully human antibodies can be obtained by using commercially available mice that have been engineered to express specific human immunoglobulin proteins. Transgenic animals that are designed to produce a more desirable (e.g., fully human antibodies) or more robust immune response may also be used for generation of humanized or human antibodies. Examples of such technology are Xenomouse® from Amgen, Inc. (Fremont, Calif.) and HuMAb-Mouse® and TC Mouse® from Medarex, Inc. (Princeton, N.J.). In another alternative, antibodies may be made recombinantly by phage display technology. See, for example, U.S. Pat. Nos. 5,565,332; 5,580,717; 5,733,743; and 6,265,150; and Winter et al., (1994) Annu. Rev. Immunol. 12:433-455. Alternatively, the phage display technology (McCafferty et al., (1990) Nature 348:552-553) can be used to produce human antibodies and antibody fragments in vitro, from immunoglobulin variable (V) domain gene repertoires from unimmunized donors.

Antigen-binding fragments of an intact antibody (full-length antibody) can be prepared via routine methods. For example, F(ab')2 fragments can be produced by pepsin digestion of an antibody molecule, and Fab fragments that can be generated by reducing the disulfide bridges of F(ab')2 fragments.

Genetically engineered antibodies, such as humanized antibodies, chimeric antibodies, single-chain antibodies, and bi-specific antibodies, can be produced via, e.g., conventional recombinant technology. In one example, DNA encoding a monoclonal antibodies specific to a target antigen can be readily isolated and sequenced using conventional procedures (e.g., by using oligonucleotide probes that are capable of binding specifically to genes encoding the heavy and light chains of the monoclonal antibodies). The hybridoma cells serve as a preferred source of such DNA. Once isolated, the DNA may be placed into one or more expression vectors, which are then transfected into host cells such as *E. coli* cells, simian COS cells, Chinese hamster ovary (CHO) cells, or myeloma cells that do not otherwise produce immunoglobulin protein, to obtain the synthesis of monoclonal antibodies in the recombinant host cells. See, e.g., PCT Publication No. WO 87/04462. The DNA can then be modified, for example, by substituting the coding sequence for human heavy and light chain constant domains in place of the homologous murine sequences, Morrison et al., (1984) *Proc. Nat. Acad. Sci.* 81:6851, or by covalently joining to the immunoglobulin coding sequence all or part of the coding sequence for a non-immunoglobulin polypeptide. In that manner, genetically engineered antibodies, such as "chimeric" or "hybrid" antibodies; can be prepared that have the binding specificity of a target antigen.

Techniques developed for the production of "chimeric antibodies" are well known in the art. See, e.g., Morrison et al. (1984) *Proc. Natl. Acad. Sci. USA* 81, 6851; Neuberger et al. (1984) *Nature* 312, 604; and Takeda et al. (1984) *Nature* 314:452.

Methods for constructing humanized antibodies are also well known in the art. See, e.g., Queen et al., *Proc. Natl. Acad. Sci. USA,* 86:10029-10033 (1989). In one example, variable regions of $V_H$ and $V_L$ of a parent non-human antibody are subjected to three-dimensional molecular modeling analysis following methods known in the art. Next, framework amino acid residues predicted to be important for the formation of the correct CDR structures are identified using the same molecular modeling analysis. In parallel, human $V_H$ and $V_L$ chains having amino acid sequences that are homologous to those of the parent non-human antibody are identified from any antibody gene database using the parent $V_H$ and $V_L$ sequences as search queries. Human $V_H$ and $V_L$ acceptor genes are then selected.

The CDR regions within the selected human acceptor genes can be replaced with the CDR regions from the parent non-human antibody or functional variants thereof. When necessary, residues within the framework regions of the parent chain that are predicted to be important in interacting with the CDR regions (see above description) can be used to substitute for the corresponding residues in the human acceptor genes.

A single-chain antibody can be prepared via recombinant technology by linking a nucleotide sequence coding for a heavy chain variable region and a nucleotide sequence coding for a light chain variable region. Preferably, a flexible linker is incorporated between the two variable regions. Alternatively, techniques described for the production of single chain antibodies (U.S. Pat. Nos. 4,946,778 and 4,704,692) can be adapted to produce a phage scFv library and scFv clones specific to TLR-4 can be identified from the library following routine procedures. Positive clones can be subjected to further screening to identify those that suppress TLR-4 activity.

Antibodies obtained following a method known in the art and described herein can be characterized using methods well known in the art. For example, one method is to identify the epitope to which the antigen binds, or "epitope mapping." There are many methods known in the art for mapping and characterizing the location of epitopes on proteins, including solving the crystal structure of an antibody-antigen complex, competition assays, gene fragment expression assays, and synthetic peptide-based assays, as described, for example, in Chapter 11 of Harlow and Lane, Using Antibodies, a Laboratory Manual, Cold Spring Harbor Laboratory Press, Cold Spring Harbor, N.Y., 1999. In an additional example, epitope mapping can be used to determine the sequence to which an antibody binds. The epitope can be a linear epitope, i.e., contained in a single stretch of amino acids, or a conformational epitope formed by a three-dimensional interaction of amino acids that may not necessarily be contained in a single stretch (primary structure linear sequence). Peptides of varying lengths (e.g., at least 4-6 amino acids long) can be isolated or synthesized (e.g., recombinantly) and used for binding assays with an antibody. In another example, the epitope to which the antibody binds can be determined in a systematic screening by using overlapping peptides derived from the target antigen sequence and determining binding by the antibody. According to the gene fragment expression assays, the open reading frame encoding the target antigen is fragmented either randomly or by specific genetic constructions and the reactivity of the expressed fragments of the antigen with the antibody to be tested is determined. The gene fragments may, for example, be produced by PCR and then transcribed and translated into protein in vitro, in the presence of radioactive amino acids. The binding of the antibody to the radioactively labeled antigen fragments is then determined by immunoprecipitation and gel electrophoresis. Certain epitopes can also be identified by using large libraries of random peptide sequences displayed on the surface of phage particles (phage libraries). Alternatively, a defined library of overlapping peptide fragments can be tested for binding to the test antibody in simple binding assays. In an additional example, mutagenesis of an antigen binding domain, domain swapping experiments and alanine scanning mutagenesis can be performed to identify residues required, sufficient, and/or necessary for epitope binding. For example, domain swapping experiments can be performed using a mutant of a target antigen in which various fragments of the TLR-4 polypeptide have been replaced (swapped) with sequences from a closely related, but antigenically distinct protein (such as another member of the neurotrophin protein family). By assessing binding of the antibody to the mutant TLR-4, the importance of the particular antigen fragment to antibody binding can be assessed.

Alternatively, competition assays can be performed using other antibodies known to bind to the same antigen to determine whether an antibody binds to the same epitope as the other antibodies. Competition assays are well known to those of skill in the art.

TLR-4 antagonists other than antibodies capable of interfering with the TLR-4 signaling pathway as described above can be used in the methods described herein.

In some embodiments of the invention, the TLR-4 antagonist comprises at least one antisense nucleic acid molecule capable of blocking or decreasing the expression of a functional TLR-4 (e.g., a human TLR-4). Nucleotide sequences of TLR-4 genes are known and are readily available from publicly available databases. See above disclosures. It is routine to prepare antisense oligonucleotide molecules that will specifically bind a target mRNA without cross-reacting with other polynucleotides. Exemplary sites of targeting include, but are not limited to, the initiation codon, the 5' regulatory regions, the coding sequence and the 3' untranslated region. In some embodiments, the oligonucleotides are about 10 to 100 nucleotides in length, about 15 to 50 nucleotides in length, about 18 to 25 nucleotides in length, or more. The oligonucleotides can comprise backbone modifications such as, for example, phosphorothioate linkages, and 2'-0 sugar modifications well known in the art.

Alternatively, TLR-4 expression and/or release can be decreased using gene knockdown, morpholino oligonucleotides, small interfering RNA (siRNA or RNAi), microRNA or ribozymes, methods that are well-known in the art. RNA interference (RNAi) is a process in which a dsRNA directs homologous sequence-specific degradation of messenger RNA. In mammalian cells, RNAi can be triggered by 21-nucleotide duplexes of small interfering RNA (siRNA) without activating the host interferon response. The dsRNA used in the methods disclosed herein can be a siRNA (containing two separate and complementary RNA chains) or a short hairpin RNA (i.e., a RNA chain forming a tight hairpin structure), both of which can be designed based on the sequence of the target gene. Alternatively, it can be a microRNA.

Optionally, a nucleic acid molecule to be used in the method described herein (e.g., an antisense nucleic acid, a small interfering RNA, or a microRNA) as described above contains non-naturally-occurring nucleobases, sugars, or covalent internucleoside linkages (backbones). Such a modified oligonucleotide confers desirable properties such as enhanced cellular uptake, improved affinity to the target nucleic acid, and increased in vivo stability.

In one example, the nucleic acid has a modified backbone, including those that retain a phosphorus atom (see, e.g., U.S. Pat. Nos. 3,687,808; 4,469,863; 5,321,131; 5,399,676; and 5,625,050) and those that do not have a phosphorus atom (see, e.g., U.S. Pat. Nos. 5,034,506; 5,166,315; and 5,792,608). Examples of phosphorus-containing modified backbones include, but are not limited to, phosphorothioates, chiral phosphorothioates, phosphorodithioates, phosphotriesters, aminoalkyl-phosphotriesters, methyl and other alkyl phosphonates including 3'-alkylene phosphonates, 5'-alkylene phosphonates and chiral phosphonates, phosphinates, phosphoramidates including 3'-amino phosphoramidate and aminoalkylphosphoramidates, thionophosphoramidates, thionoalkylphosphonates, thionoalkylphosphotriesters, selenophosphates and boranophosphates having 3'-5' linkages, or 2'-5' linkages. Such backbones also include those having inverted polarity, i.e., 3' to 3', 5' to 5' or 2' to 2' linkage. Modified backbones that do not include a phosphorus atom are formed by short chain alkyl or cycloalkyl internucleoside linkages, mixed heteroatom and alkyl or cycloalkyl internucleoside linkages, or one or more short chain heteroatomic or heterocyclic internucleoside linkages. Such backbones include those having morpholino linkages (formed in part from the sugar portion of a nucleoside); siloxane backbones; sulfide, sulfoxide and sulfone backbones; formacetyl and thioformacetyl backbones; methylene formacetyl and thioformacetyl backbones; riboacetyl backbones; alkene containing backbones; sulfamate backbones; methyleneimino and methylenehydrazino backbones; sulfonate and sulfonamide backbones; amide backbones; and others having mixed N, O, S and $CH_2$ component parts.

In another example, the nucleic acid used in the disclosed methods includes one or more substituted sugar moieties. Such substituted sugar moieties can include one of the following groups at their 2' position: OH; F; O-alkyl, S-alkyl, N-alkyl, O-alkenyl, S-alkenyl, N-alkenyl; O-alkynyl, S-alkynyl, N-alkynyl, and O-alkyl-O-alkyl. In these groups, the alkyl, alkenyl and alkynyl can be substituted or unsubstituted $C_1$ to $C_{10}$ alkyl or $C_2$ to $C_{10}$ alkenyl and alkynyl. They may also include at their 2' position heterocycloalkyl, heterocycloalkaryl, aminoalkylamino, polyalkylamino, substituted silyl, an RNA cleaving group, a reporter group, an intercalator, a group for improving the pharmacokinetic properties of an oligonucleotide, or a group for improving the pharmacodynamic properties of an oligonucleotide. Preferred substituted sugar moieties include those having 2'-methoxyethoxy, 2'-dimethylaminooxyethoxy, and 2'-dimethylaminoethoxyethoxy. See Martin et al., Helv. Chim. Acta, 1995, 78, 486-504.

In yet another example, the nucleic acid includes one or more modified native nucleobases (i.e., adenine, guanine, thymine, cytosine and uracil). Modified nucleobases include those described in U.S. Pat. No. 3,687,808, The Concise Encyclopedia Of Polymer Science And Engineering, pages 858-859, Kroschwitz, J. I., ed. John Wiley & Sons, 1990, Englisch et al., Angewandte Chemie, International Edition, 1991, 30, 613, and Sanghvi, Y. S., Chapter 15, Antisense Research and Applications, pages 289-302, CRC Press, 1993. Certain of these nucleobases are particularly useful for increasing the binding affinity of the antisense oligonucleotide to its target nucleic acid. These include 5-substituted pyrimidines, 6-azapyrimidines and N-2, N-6 and O-6 substituted purines (e.g., 2-aminopropyl-adenine, 5-propynyluracil and 5-propynylcytosine). See Sanghvi, et al., eds., Antisense Research and Applications, CRC Press, Boca Raton, 1993, pp. 276-278).

Any of the nucleic acids can be synthesized by methods known in the art. See, e.g., Caruthers et al., 1992, Methods in Enzymology 211, 3-19, Wincott et al., 1995, Nucleic Acids Res. 23, 2677-2684, Wincott et al., 1997, Methods Mol. Bio. 74, 59, Brennan et al., 1998, Biotechnol Bioeng., 61, 33-45, and Brennan, U.S. Pat. No. 6,001,311. It can also be transcribed from an expression vector and isolated using standard techniques.

In other embodiments, the TLR-4 antagonist comprises at least one TLR-4 inhibitory compound. As used herein, "TLR-4 inhibitory compound" refers to a compound other than an anti-TLR-4 antibody that directly or indirectly reduces, inhibits, neutralizes, or abolishes TLR-4 biological activity. An TLR-4 inhibitory compound should exhibit any one or more of the following characteristics: (a) binds to TLR-4 and inhibits its biological activity and/or downstream pathways mediated by TLR-4 signaling function; (b) reduces the blood glucose level in a subject, (c) enhances insulin level in a subject, and/or (e) alleviating one or more complications associated with diabetes. One skilled in the art can identify and prepare such inhibitory compounds.

In other embodiments, the TLR-4 inhibitory compounds described herein are small molecules, which can have a molecular weight of about any of 100 to 20,000 daltons, 500 to 15,000 daltons, or 1000 to 10,000 daltons. Libraries of small molecules are commercially available. The small molecules can be administered using any means known in the art, including inhalation, intraperitoneally, intravenously, intramuscularly, subcutaneously, intrathecally, intraventricularly, orally, enterally, parenterally, intranasally, or dermally. In general, when the TLR-4-antagonist according to the invention is a small molecule, it will be administered at the rate of 0.1 to 300 mg/kg of the weight of the patient divided into one to three or more doses. For an adult patient of normal weight, doses ranging from 1 mg to 5 g per dose can be administered.

The above-mentioned small molecules can be obtained from compound libraries. The libraries can be spatially addressable parallel solid phase or solution phase libraries. See, e.g., Zuckermann et al., *J. Med. Chem.* 37, 2678-2685, 1994; and Lam Anticancer Drug Des. 12:145, 1997. Methods for the synthesis of compound libraries are well known in the art, e.g., DeWitt et al. PNAS USA 90:6909, 1993; Erb et al. PNAS USA 91:11422, 1994; Zuckermann et al. J. Med. Chem. 37:2678, 1994; Cho et al. Science 261:1303, 1993;

Carrell et al. Angew Chem. Int. Ed. Engl. 33:2059, 1994; Carell et al. Angew Chem. Int. Ed. Engl. 33:2061, 1994; and Gallop et al. J. Med. Chem. 37:1233, 1994. Libraries of compounds may be presented in solution (e.g., Houghten Biotechniques 13:412-421, 1992), or on beads (Lam Nature 354:82-84, 1991), chips (Fodor Nature 364:555-556, 1993), bacteria (U.S. Pat. No. 5,223,409), spores (U.S. Pat. No. 5,223,409), plasmids (Cull et al. PNAS USA 89:1865-1869, 1992), or phages (Scott and Smith Science 249:386-390, 1990; Devlin Science 249:404-406, 1990; Cwirla et al. PNAS USA 87:6378-6382, 1990; Felici J. Mol. Biol. 222: 301-310, 1991; and U.S. Pat. No. 5,223,409).

Exemplary TLR-4 inhibitory compounds include, but are not limited to (1) TLR4-IN-C34, which is an aminomonosaccharide that inhibits TLR4 signaling by docking with the hydrophobic pocket of the MD2 (Matthew D et al., PLoS One (2013) 8:e65779), (2) NBP2-26244, which is a peptide that inhibits TLR4 signaling by blocking interactions between TLR4 and its intracellular adaptor protein (Mal/TIRAP and TRAM) (Lysakova-Devine T et al., J Immunol. (2010) 185:4261), and (3) CLI-095 which is a cyclohexene derivative that inhibits TLR4 signaling by blocking the intracellular domain of TLR4, but not the extracellular domain (Li M et al., Mol. Pharmacol (2006) 69:1288-95).

The present invention is further illustrated by the following examples, which are provided for the purpose of demonstration rather than limitation. Those of skill in the art should, in light of the present disclosure, appreciate that many changes can be made in the specific embodiments which are disclosed and still obtain a like or similar result without departing from the spirit and scope of the invention.

Without further elaboration, it is believed that one skilled in the art can, based on the above description, utilize the present invention to its fullest extent. The following specific embodiments are, therefore, to be construed as merely illustrative, and not limitative of the remainder of the disclosure in any way whatsoever. All publications cited herein are incorporated by reference for the purposes or subject matter referenced herein.

EXAMPLES

In present invention, we found a truncated form (a synthetic peptide), lacking domains 1-3, from *streptococcus pneumoniae* that is effective in controlling type II diabetic and its related consequence of atherosclerosis and obesity under high fat diet model. The PLY peptide of the present invention acts as a Toll-like receptor 4 (TLR4) antagonist but without hemolytic effect as the full-length Ply. No trigger of cell apoptosis and cytotoxicity was observed. The PLY peptide of the present invention shows an effectiveness on blood glucose control and increased production of insulin in both high diet induced rat model and diabetic knockout (db/db$^{-/-}$) mice model. Significant change in ICAM-1, VCAM-1 and E-selectin expression between control and treatment group was observed in animal model. The PLY peptide of the present invention shows an inhibitory effect of LPS activated neutrophil transmigration in HUVAC, cytoprotective effect under low shear stress of laminar flow and reduces murine atherosclerotic inflammation.

1. Materials and Methods
1.1 Pneumolysin (PLY), Full Length and Fragments Thereof The full length pneumococcal pneumolysin (PLY, 1-471 amino acid residues) and fragments thereof, including a fragment of domain 4 (PLY4, 360-471 amino acid residues), a C-terminal 70 amino acid fragment (C70PLY4, 402-471 amino acid residues), a N-terminal 35 amino acid fragment of C70PLY4 (N35PLY4, 402-436 amino acid residues), a N-terminal 35 amino acid fragment of C70PLY4 with one mutation (N35PLY4m25K), a N-terminal 35 amino acid fragment of C70PLY4 with two mutation (N35PLY4m24L25K), and a N-terminal 50 amino acid fragment of C70PLY4 with deletion of first 5 amino acid residues (M50PLY4), as shown in above Table 1, were produced and analyzed in the subsequent assays.

1.2 Cloning, Expression and Production of Recombinant Domain 4 of Pneumolysin (rPly4)

The Ply4 gene was amplified using the forward 5'-GGAATTCCATATGAACGGAGATTTACTGCTG-3' (SEQ ID NO: 15) primer containing a Nde I restriction site and the reverse primer, 5'-CCGCTCGAGGTCATTTTC-TACCTTATCTTCTAC-3' (SEQ ID NO: 16) complementary to the coding sequence and containing a Xho I restriction site. As a result, the C-terminal end of the recombinant protein contains an additional histidine tag, LEHHHHHH (SEQ ID NO: 17). The PCR product was cloned into the expression vector, pET-22b (+) (Novagen, Madison, Wis., USA) using Nde I and Xho I sites, resulting in plasmid pPly4.

The Ply4 gene was expressed in BL21 (DE3) Star from Novagen (Madison, Wis., USA). The expression of recombinant Ply4 (rPly4) was induced with 1 mM of IPTG at 37° C. overnight, and cells were harvested by centrifugation.

After induction of rPly4, 3.6 liters of cell culture were centrifuged (6400×g for 15 min) and the pellets were re-suspended in 360 mL of phosphate-buffered saline (PBS) buffer containing 10 mM imidazole, pH7.6. After disruption of the cells in a French Press (Constant Systems, Daventry, UK) at 27 Kpsi, cell lysates were clarified by ultracentrifugation (10,000×g for 60 min). The supernatant was loaded onto a 9 mL Ni-NTA resin (Qiagen, San Diego, Calif., USA). The column (1.1 cm i.d.×9.5 cm) was first washed with the homogenization buffer followed by the same buffer containing 40 mM imidazole. The rPly4 was then eluted with the homogenization buffer containing 500 mM imidazole. A polymyxin B agarose column (Pierce, Rockfold, Ill., USA) was used to remove lipopplysaccharide (LPS). The amount of residual LPS in each target proteins was determined by the Limulus amebocyte lysate (LAL) assay (Associates of Cape Cod, Inc., Cape Cod, Mass., USA). LPS levels were found to be below 3 EU/mg.

The full length PLY was prepared by recombinant technology in a similar manner.

1.3 Synthesis of Peptides

Various PLY fragments were synthesized via a solid phase method using an automated peptide synthesizer (model PS-3 from Protein Technologies, Inc.) employing the fluorenylmethoxycarbonyl (Fmoc) group for α-amino group protection. The resin used is derived from NovaSyn TGR resin with the modified Rink linker (Merck, Darmstadt, Germany). Tryptophan and lysine residues were protected with the tert-butoxycarbonyl (tBoc) and arginine residues were protected with 2,2,4,6,7-pentamethyldihydrobenzofuran-5-sulfonyl (Pbf) group. The final de-blocking step was carried out with a mixture of TFA/Triisopropylsilane/water (94:3:3). The crude peptides were recovered by precipitation with diethyl ether as non-solvent and characterized by analytical reversed-phase HPLC. Mass spectrometry analyses were performed on a Agilent 1100 Series LC/MSD high performance ion trap mass spectrometer to ensure the target peptide is obtained. The C70PLY4 was synthesized by Almac Sciences, UK. Other PLY peptides were synthesized in this manner.

1.4 High Fat Diet (HFD)-Induced Type 2 Diabetic Rats

The Sprague-Dawley rats were allocated to two dietary regimens by feeding either normal or HFD ad libitum, for the initial period of 2 weeks. After 2 weeks of dietary manipulation, the group of rats fed HFD were injected intraperitoneally (i.p.) with a low dose of STZ (35 mg/kg b.w.), while the respective control rats were given vehicle citrate buffer (pH 4.5) in a dose volume of 1 mL/kg, i.p. Seven days after STZ injection, rats were screened for blood glucose levels. Overnight fasted (10-12 hours) animals were given glucose (3 g/kg b.w.) by gastric intubation. After 2 hours of oral administration, blood samples were taken from lateral tail vein, left to coagulate and centrifuged; then serum glucose concentration was measured. Rats having serum glucose ≥200 mg/dL after 2 hours of glucose intake were considered diabetic and selected for further pharmacological studies. The rats were allowed to continue to feed on their respective diets until the end of the study (16).

The experimental animals were divided into three groups, each group comprising six rats designated as follows: (1) group 1 served as control rats (non-DM control); (2) group 2 served as diabetic control rats (STZ+vehicle); and (3) group 3 served as diabetic treatment rats administered with C70PLY4 (2 mg/kg/3 days) in aqueous suspension i.p. for 30 days (STZ+C70PLY4). By the end of the experiment, animals were sacrificed and blood samples, muscle and liver were obtained.

1.5 Diabetic Gene Knockout Mice (C57BL/KsJ-db/db)

Male C57BL/KsJ-db/db mice (diabetic deficiency knockout mice) at 5 weeks of age (23 g) were fed a pelletized commercial chow diet for acclimation from the arrival for 2 weeks. All mice were maintained under a controlled light/dark cycle (12:12 h, lights on at 8:00 AM) and constant temperature (25° C.). They were given free access to food and distilled water, and the food consumption and body weight gain were measured daily and weekly, respectively. Animals were randomly divided into two groups, each group comprising six mice designated as follows: (1) group 1 served as control mice (vehicle); and (2) group 2 served as diabetic mice administered C70PLY4 (2 mg/kg/3 days) in aqueous suspension i.p. for 30 days (C70PLY4). By the end of the experiment, all the mice were anesthetized with ketamine after a 12-h fast, and blood samples were collected from the inferior vena cava into heparin-coated tube. The blood was centrifuged at 1000 g for 15 min at 4° C., and plasma and erythrocyte were separated. The livers and adipose tissues were removed, washed, weighted, and frozen at −70° C. until analyzed.

1.6 Measurement of Glucose Level

Blood Glucose Test Strips and Blood Glucose Monitoring System were used to determine whole blood glucose levels on a drop of tail blood collected between 10 am and midday. Glucose concentration was determined colorimetrically using a glucose oxidase/peroxidase reagent kit. Samples were incubated with 100 µl of assay reagent at 37° C. for 30 min and measured at 540 nm. Values were expressed in mg/dL.

1.7 ELISA Assays

The levels of insulin, sICAM-1, sVCAM-1, and E-selectin in serum were determined by using sandwich ELISA (R&D) according to manufacturer's protocols.

1.8 Pathology of Aorta in Mice by Hematoxylin and Eosin (HE) Stain

The ascending part of aorta were taken from mice, including control health mice and HFD induced diabetic mice, with and without treatment of C70PLY4, and kept in 10% formalin buffered for 24 h. The specimens were routinely embedded in paraffin blocks and cut in transversal sections (3 µm). The slides were stained with hematoxylin and eosin. The specimens were analyzed with light microscope.

1.9 TLR4-Deficient [TLR4(−/−)] C3H/HeJ Mice and Wild Type C3H/HeN Mice

To obtain mice neutrophils from TLR4-deficient [TLR4(−/−)] C3H/HeJ mice and wild type C3H/HeN mice, inflammation was induced by 0.1 ml of uric acid solution into the peritoneal cavity of the mouse. The uric acid solution (noncrystalline form) was prepared by mixing with saline (10% [wt/vol]) and sonicated for 10 min. Immediately before inoculation, the milky white precipitated uric acid solution was shaken vigorously. Peritoneal exudate cells were harvested 4, 18, or 24 h after injection by two lavages of the peritoneal cavity with 5 ml of cold phosphate-buffered saline (PBS; total volume, 10 ml). Uric acid-induced peritoneal cells (UAPMN) were washed by centrifugation at 200×g for 10 min at 4° C. Followed by hypotonic lysis to eliminate red blood cells, centrifugation and an additional wash were performed. The cells were then resuspended in Krebs-Ringer phosphate buffer (KRG; pH 7.3). The numbers and populations of peritoneal exudate cells were determined by staining the nuclei with Turk reagent and by cytospin centrifugation followed by May-Grünwald-Giemsa staining, respectively. Uric acid injection into the peritoneal cavity gave a yield of 1 to $2\times10^7$ cells/mouse depending on time of incubation (4 hr). The levels of purity of the uric acid-induced PMN were 95% after 4 h postinjection. Viability of the isolated neutrophils exceeded 95% as determined by trypan blue exclusion. The PMN from TLR4(−/−) C3H/HeJ mice and wild type C3H/HeN mice were then used for PMN transmigration Assay.

1.10 Human Umbilical Vein Endothelial Cell (HUVEC) Culture

HUVEC was purchased by ScienCell Research Laboratories (CA, USA). The pellet was resuspended in M199 culture medium supplemented with penicillin/streptomycin and 20% fetal bovine serum (FBS), after which the cells were plated onto cell culture dishes. ECs were grown in Petri dishes for three days and then seeded onto glass slides pre-coated with rat tail type I collagen. Secondary cultures were used for the experiments within two days after reaching confluence (~1-$2\times10^5$ cells/cm$^2$).[12]

1.11 Isolation of Human and Mouse Polymorphonuclear Leukocyte (PMNs)

Neutrophils from human were isolated blood that was drawn in a syringe containing preservative-free heparin (20 U/ml final), and mixed with an equal volume of PBS containing 3% dextran and then incubated for 20 min at room temperature. The leukocyte-rich plasma (upper layer) was collected and pellet cells was obtained from the plasma by centrifuge and resuspended in 0.9% NaCl. Layer 10 ml Ficoll-Hypaque solution beneath the cell suspension. After centrifuge 1500×g for 20 min, aspirate the Ficoll-Hypaque layer, leaving the neutrophil/RBC pellet. Cells were subjected to hypotonic lysis by resuspending each neutrophil/RBC pellet in cold 0.2% NaCl for 30 sec. At the end of this period, restore isotonicity by adding ice-cold 1.6% NaCl. After centrifuge, resuspend cells in ice-cold PBS/glucose buffer. Neutrophils from mice were isolated from the peritoneum as previously described. See, e.g., Rabes et al., Curr Top Microbiol Immunol 397:215-227 (2016). The cell concentration was adjusted to 16,107 cells/mL. The viability of the isolated neutrophils exceeded 95%, as determined by Trypan blue exclusion.

1.12 PMNs Transendothelial Migration

Transendothelial migration was performed by using a Transwell system. Transwell filters were pre-seeded with HUVEC monolayers for 24 hrs and transferred to clean 24-well plates. HUVECs were washed twice with DPBS, 500 µl of ECM was added to the Transwell filter compartment and $10^6$ neutrophils were then added in upper chamber. Transendothelial migration was stimulated by addition of LPS to the lower chamber to a final concentration of 1 µg/ml. Cells were incubated with the endothelial cells for 1 h at 37° C. At the conclusion of the incubation, migrated cells were collected from the lower chamber and counted in a hemacytometer in triplicate. Percent PMN transmigration was calculated by dividing the number of PMN recovered from the lower chamber by the number of PMN initially added.

1.13 In Vitro Protein Binding Assay for MD2 and Toll-Like Receptor (TLR) 4

The recombinant TLR4 protein was diluted in phosphate buffer saline (PBS) (2 µg/mL) and immobilized on a 96-well (100 ng/well) enzyme-linked immunosorbent assay (ELISA) plate by incubation at 37° C. for 2 h. The wells were washed three times with PBS, followed by blocking with the addition of 300 µL 5% bovine serum albumin (BSA) in PBS at ambient temperature overnight. Then, the plate was washed three times with PBST (PBS with 0.05% Tween 20 solution) before the addition of the recombinant MD2 protein solutions at various concentrations (2-fold serial dilution from 133.3 to 0.065 nM). The ligands (MD2) and TLR4 proteins were incubated at 37° C. for 2 h, and the plate was then washed three times with PBST, followed by the addition of 100 µL anti-MD2 antibodies diluted in 1% BSA (1:1000). After incubation at ambient temperature for 1 h, the plate was washed with PBST three times, followed by the addition of 100 µL anti-mouse IgG-HRP antibodies diluted in 1% BSA (1:2000). After incubation at ambient temperature for 1 h, the plate was washed with PBST three times, followed by the addition of 100 µL of the HRP substrate (i.e. 3,3',5,5'-tetramethylbenzidine, TMB) to each well. The reaction was terminated after 5 min at ambient temperature by the addition of 50 µL of the stop solution (2 N $H_2SO_4$) to each well. The optical density ($OD_{450}$) in each well was determined using an ELISA plate reader. The binding affinity in nM was computed using GraphPad Prism (GraphPad Software, San Diego, Calif.) by nonlinear regression analysis.

1.14 In Vitro Protein Competition Binding Assay (C70PLY4, N35PLY4, and M50PLY4 for MD2/TLR4 Interaction)

The recombinant TLR4 protein was diluted in PBS (2 µg/mL) and immobilized on a 96-well (100 ng/well) ELISA plate by incubation at 37° C. for 2 h. The wells were washed three times with PBS, followed by blocking with the addition of 300 µL 5% BSA in PBS at ambient temperature overnight. Then, the plate was rewashed three times with PBST before performed competition binding assay. The binding of MD2 (50 nM) to TLR4 was competed by adding various amounts (2-fold serial dilution from 50 µM to 3.05 nM) of C70PLY4, N35PLY4, or M50PLY4 peptide, and the residual binding was examined using anti-MD2 and anti-mouse-IgG-HRP antibodies diluted in 1% BSA as described in herein.

1.15 Western Blot Analysis.

Cells were kept as the control, treated with LPS (1 µg/mL), or co-treated with LPS (1 µg/mL) and C70PLY4 (100, 300, and 500 nM) for 24 h and the phosphorylation of ERK1/2 and NFκB-p65 subunit were determined by Western blot. Cells were collected by scraping and lysed with RIPA buffer containing 1% NP-40, 0.5% sodium deoxycholate, 0.1% SDS, and a protease inhibitor mixture (PMSF, aprotinin, and sodium orthovanadate). The total cell lysate (50 µg of protein) was separated by SDS-polyacrylamide gel electrophoresis (PAGE) (10% running, 4% stacking) and transferred onto a polyvinylidene fluoride membrane (Immobilon P, 0.45-µm pore size). The membrane was then incubated with the designated antibodies. Immunodetection was performed by using the Western-Light chemiluminescent detection system (Applied Biosystems, Foster City, Calif.).

1.16 Shear Stress Experiment

HUVECs was mounted on a slide in a parallel-plate flow chamber, which was connected to a perfusion loop system (15). The system was kept in a constant-temperature, maintained at pH 7.4 by gassing with 5% $CO_2$. The osmolality of the medium was kept in the range 285-295 mOsm/kg during perfusion. The flow channel width (w) was 1 cm and the channel height (h) was 0.025 cm. The fluid shear stress ($\tau$) performed on the HUVECs was estimated by using the formula, $\tau=6$ µQ/wh2, where µ is the viscosity of the medium and Q is the flow rate. The fluid shear stress applied in this study was 4 dynes/$cm^2$. Cells were mounted on the slide and incubated with M199 media in the presence or absence of 100 mM various PLY peptides, at 37° C., 5% $CO_2$ for 1 hour, and then exposed to the shear stress of 4 dyn/$cm^2$ for 6 hours. Control cells were incubated with static medium for the same time.

1.17 Immunofluorescence Microscopy

After exposing to shear stress with or without peptide treatment, HUVECs were washed, fixed with 4% formaldehyde, and permeabilized by 1% Triton X-100 in PBS at 37° C. for 30 min. Cells were then blocked by 10% bovine serum albumin (BSA) with 0.1% Triton X-100 in PBS for 1 hr. Intracytoplasmic F-actin immunofluorescence was detected by staining with phalloidin-fluorescein isothiocyanate (FITC) (1:1000 eBioscience) for 1 hr at room temperature, and cell nuclear stained with 4',6-diamidino-2-phenylindole (DAPI) for 10 min at room temperature. Fluorescent cells were photographed by a fluorescence microscope with CCD (OLYMPUS).

1.18 Cell Viability Assay

Cell viability was detected by a methanethiosulfonate (MTS) assay. In brief, $2\times10^4$ HUVECs were seeded to a 48-well plates in 100 µl endothelial cell medium (ECM, ScienCell Research Laboratory, Cat. 1001, USA) per well and incubated for 24 hrs. The media was removed and the cells were then incubated with media having 2% fetal bovine serum (FBS), in the absence or presence of various peptides, such as PLY, PLY123, PLY4, C70PLY4 or N35PLY4, at a concentration of 1, 10 or 100 nM. After incubation for 18 hours, the media was removed and 20 µl MTS reagents (20%) were added to each well in the final volume of 100 µl and placed in incubator for 1 hours. The optical density was measured at 490 nm using a plate reader.

1.19 Cell Apoptosis

Cell apoptosis was detected by using commercial terminal deoxynucleotidyl transferase-dUTP nick end labeling (TUNEL) and caspase-3 activity kits, i.e., Apo-BrdU in Situ DNA Fragmentation Assay Kit (BioVision) and NucView™ 488 Caspase-3 Enzyme Substrate (Biotium). In brief, after incubation with M199 media in the presence or absence of 100 mM various PLY peptides, at 37° C., 5% $CO_2$ for 1 hour, HUVECs were washed with PBS and fixed with fixation buffer on ice for 20 min. Cells were then soaked in 70% alcohol for 1 hr. After 2 times of wash by washing buffer, cells were incubated in DNA labeling solution for 60 min at 37° C. Cells were then treated with rinse buffer and incubated with antibody buffer for 30 min at room temperature. The cell nuclei were stained with propidium iodide for 30 min. Samples were observed by fluorescent microscopeand photographed charge-coupled device (CCD) camera. The living cells exhibit red fluorescence and apoptotic cells are green fluorescence.

As to caspase-3 activity assay, after variant peptide treatments, HUVECs were washed by PBS. Cells were then reacted with Caspase-3 Enzyme Substrate 1 mM for 30 min at room temperature. Cells were then observed by fluorescent microscopeand photographed CCD camera. The cells with caspase-3 activity will exhibit green fluorescence.

1.20 Statistical Analysis

The results are expressed as mean±standard error of the mean (SEM). Statistical analysis was determined by using an independent Student t-test for two groups of data and analysis of variance (ANOVA) followed by Scheffe's test for multiple comparisons. P values less than 0.05 were considered significant.

2. Results 2.1 Blood Glucose and Insulin Levels in High Fat Diet (HFD)-Induced Type 2 Diabetic Rat Model The effects of C70PLY4 on blood glucose and blood insulin levels were evaluated in STZ-induced DM rats.

Figure 3:
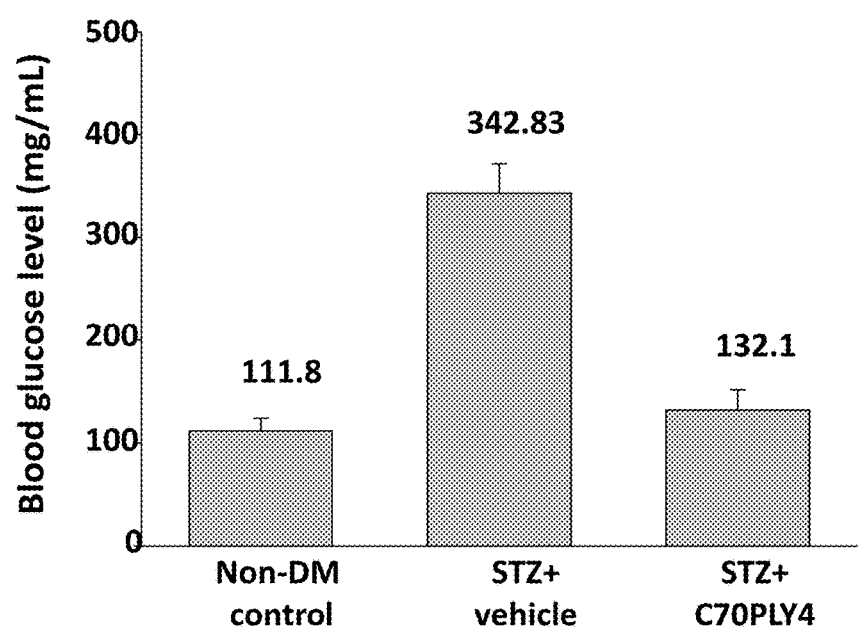
FIG. 3 shows a reduced blood glucose level in STZ-injected HFD-fed rats by treatment with C70PLY4.
Figure 4:
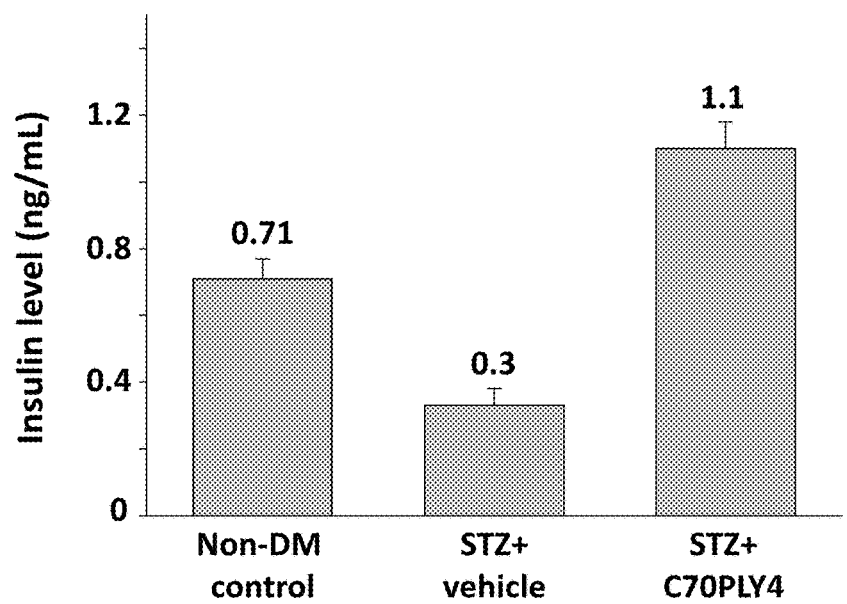
FIG. 4 shows an increased insulin level in STZ-injected HFD-fed rats by treatment with C70PLY4.

Rats given STZ+vehicle exhibited an increase in blood glucose levels and a decrease in blood insulin levels compared to non-DM control. However, STZ-injected rats administered with C70PLY4 showed decreased blood glucose and increased blood insulin levels compared to STZ-injected rats administrated with vehicle (FIG. 3 and FIG. 4). These results show that C70PLY4 has a potential effect in treating type 2 DM.

2.2 Blood Glucose and Body Weight in C57BL/KsJ-db/db Diabetic Deficiency Mice

Figure 5:
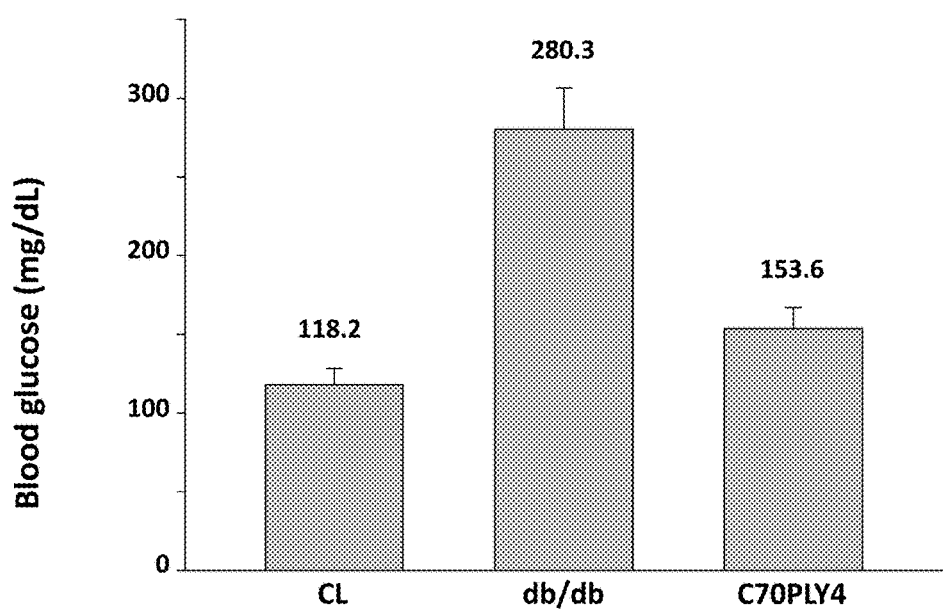
FIG. 5 shows a reduced blood glucose level in C57BL/KsJ-db/db mice by treatment with C70PLY4.
Figure 6:
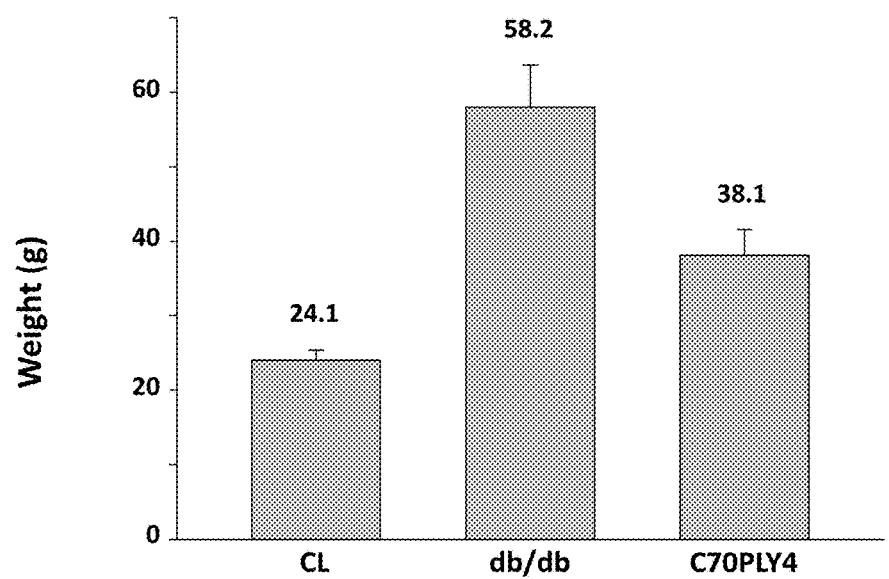
FIG. 6 shows a decreased body weight level in C57BL/KsJ-db/db mice by treatment with C70PLY4.

The C57BL/KsJ-db/db mouse has been extensively used as a spontaneous diabetic model of type 2 DM to study the pathogenesis of DM. The C57BL/KsJ-db/db mouse carries a mutation in the leptin receptor gene, an obesity-regulatory gene, and is a well-established model of obesity-induced type 2 DM mouse (22). In the present study, all C57BL/KsJ-db/db mice were diabetic when the experiment began, as indicated by the blood glucose level. The effect of C70PLY4 on the level of blood glucose and body weight was evaluated in dbldb mice. It was showed that C70PLY4 significantly decreases the blood glucose level (FIG. 5) and body weight (FIG. 6), compared with the control group, after week 2 of the experimental period. These results shows that C70PLY4 is effective in ameliorating biabetes progression.

Figure 7:
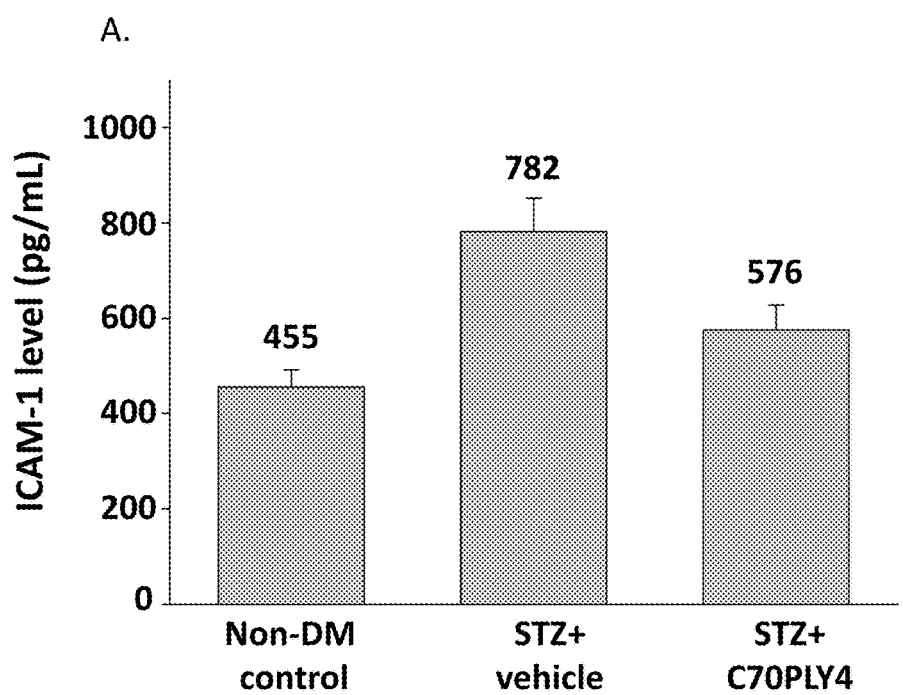
FIG. 7 includes charts showing a decreased serum soluble ICAM-1 level in STZ-injected HFD-fed rats by treatment with C70PLY4 (panel (A)); a decreased serum soluble VCAM-1 level in STZ-injected HFD-fed rats by treatment with C70PLY4 (panel (B)); and a decreased serum soluble E-selectin level in STZ-injected HFD-fed rats by treatment with C70PLY4 (panel (C)).
Figure 7:
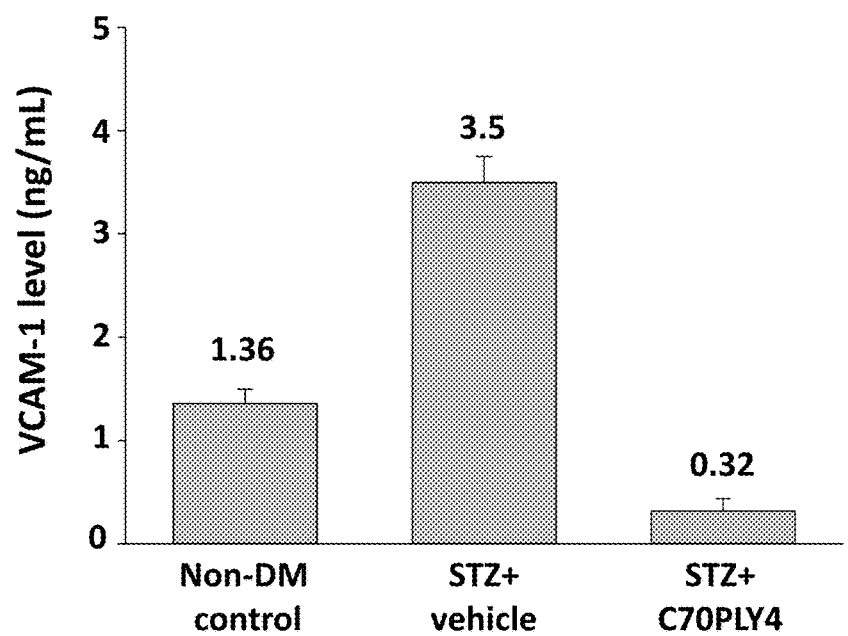
Figure 7:
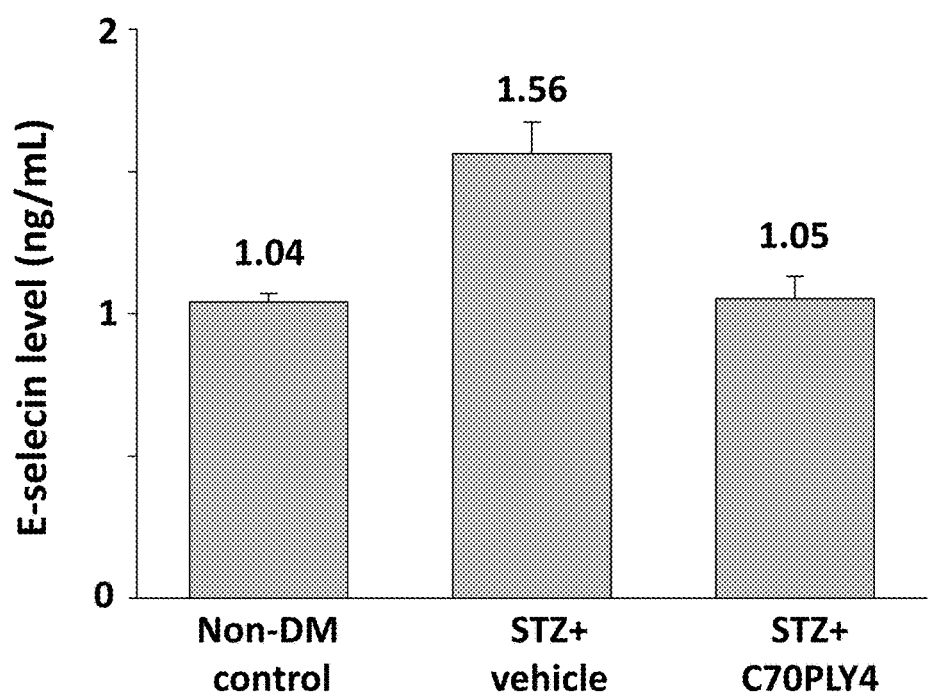

2.3 Serum Levels of sICAM-1, sVCAM-1, and sE-Selectin in HFD-Induced Type 2 Diabetic Rat Model The serum levels of ICAM-1, VCAM-1, and E-selectin are important mediators for the adhesion of leukocytes to the endothelium and significantly related to the risk of DM and associated complications, particularly atherosclerosis. We further evaluated the effect of C70PLY4 on serum levels of sICAM-1, sVCAM-1, and sE-selectin in STZ-induced DM rats. Rats given STZ and vehicle exhibited an increase in sICAM-1, sVCAM-1, and sE-selectin levels compared to non-DM control. However, rats administered with C70PLY4 in STZ-injected rats showed decreased sICAM-1 (FIG. 7, panel A), sVCAM-1(FIG. 7, panel B), and sE-selectin (FIG. 7, panel C) levels compared to STZ-injected rats administrated with vehicle. These results indicate that C70PLY4 is effective in inhibiting the production and secretion of pro-inflammatory factors in vascular cells and may play an important role in treating atherosclerosis in type 2 DM.

2.4 Anti-Atherosclerosis in STZ Rat Model

The present study determined if C70PLY4 attenuates the status of atherosclerosis in HFD-fed rats. The rats were divided into four groups: (1) control rats (non-DM group), (2) diabetic rats (STZ group, STZ is a chemical that could destroy the insulin-producing beta cells of the pancreas in mammalian and hence lead to the diabetes mellitus), (3) diabetic treatment control rats (STZ+N-acetylcycteine (NAC) group, NAC is a reduced thiol that could be used to improve the atherosclerotic status) (20), and (4) diabetic treatment rats (STZ+C70PLY4 group).

Through the HE stain, it was showed that STZ promotes the neointima formation of aorta and results in the development of atherosclerosis in STZ-treated rats. In the STZ+NAC group, NAC treatment could partially improve the STZ effect on the neointima formation. Surprisingly, in the STZ+C70PLY4 group, C70PLY4 significantly attenuated the status of neointima formation induced by STZ (FIG. 8).

Figure 9:
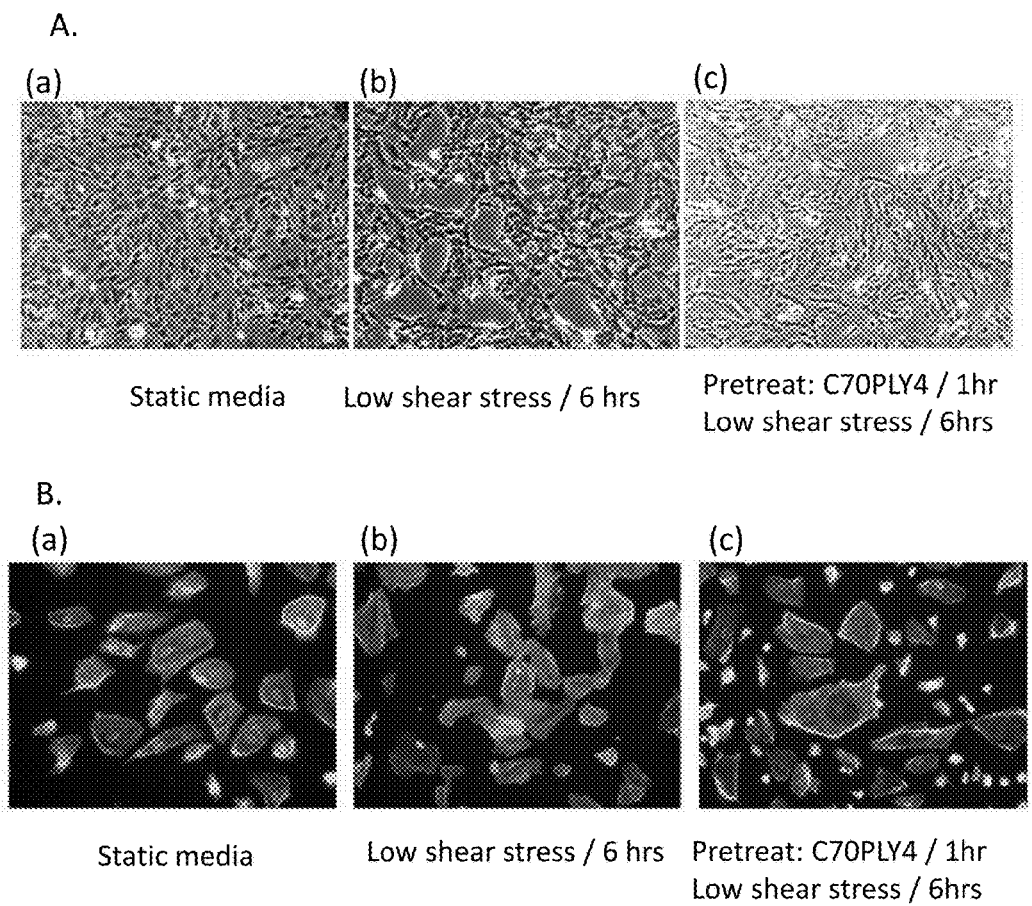
FIG. 9 shows that C70PLY4 can block the low shear stress induced morphological change (A) and cytoskeleton remodeling (B). Cells were (a) incubated in static media without PLY peptides, (b) incubated in static media without PLY peptides and then exposed to the shear stress for 6 hours, or (c) incubated in static media in the presence of C70PLY4 for 1 hour and then exposed to the shear stress for 6 hours.

2.5 The PLY Peptides Exhibit Anti-Atherosclerosis Activities under Low Shear Stress Experiment HUVEC was compared under static, low shear stress and low-shear stress with pre-treatment of C70PLY for 1 hour. Cells under 6 hours of low shear stress exhibit aggregative arrangement (FIG. 9, panel A) and remodeling of F-actin (FIG. 9, panel B); however, treatment with C70PLY4 almost block the low shear stress induced morphological change (FIG. 9, panel A) and cytoskeleton remodeling (FIG. 9, panel B). This effect of C70PLY4 can keep intact endothelium under low shear stress.

2.6 The PLY Peptides of the Present Invention Function as TLR4 Antagonists

Figure 10:
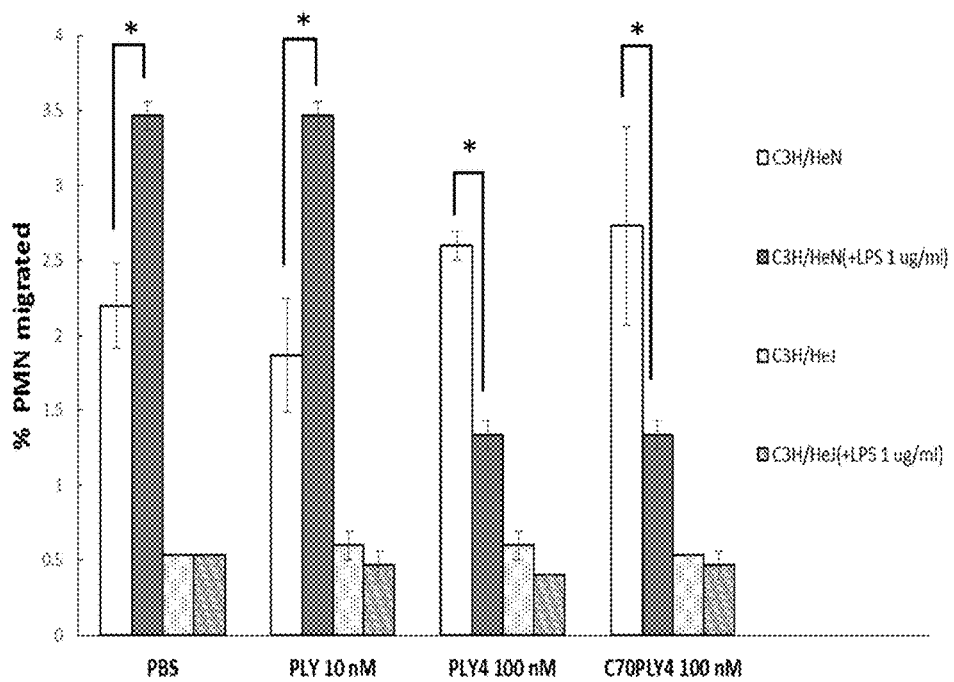
FIG. 10 shows the transmigration difference of polymorphonuclear leukocyte (PMNs) from wild type (WT) mice C3H/HeN and Toll-like receptor 4 (TLR4) deficiency mice C3H/HeJ after lipopolysaccharides stimulation.

PMN transendothelial migration plays an important role in early stage of atherogenesis. LPS is known as an inflammatory stimulator for vascular endothelial cells through activating TLR4 protein (18) To evaluate if the PLY peptides of the present invention provide the anti-atherosclerosis activities through inhibition of TLR4 activation, PMN transmigration assay was conducted in PMNs isolated from different groups of mice, including (1) C3H/HeN [wild-type (WT)] mice without LPS priming, (2) WT mice priming with 1 μg LPS, and (3) TLR4(−/−) mice C3H/HeJ with or without LPS priming. In comparing the results obtained in PMNs isolated from C3H/HeN [wild-type (WT)] mice without LPS priming, PMNs isolated from WT priming with 1 μg LPS showed a significant increasing transendothelial cell migration but not with PMNs isolated from TLR4(−/−) mice C3H/HeJ with or without LPS priming (FIG. 10). This result suggested that the increasing cell migration was through TLR4 pathway and increasing cell migration was stimulated by LPS, a TLR4 ligand.

The addition of full-length PLY did not affect the PMNs migration in both WT and TLR4(−/−) mice model. However, a significant inhibition of PMNs cell migration was observed with the additional PLY4 and C70PLY4 in WT mice model while this phenomenon did not occur in TLR4(−/−) mice model (FIG. 10). This result indicated that PLY4 and C70PLY4 functioned as a TLR4 antagonists.

Figure 11:
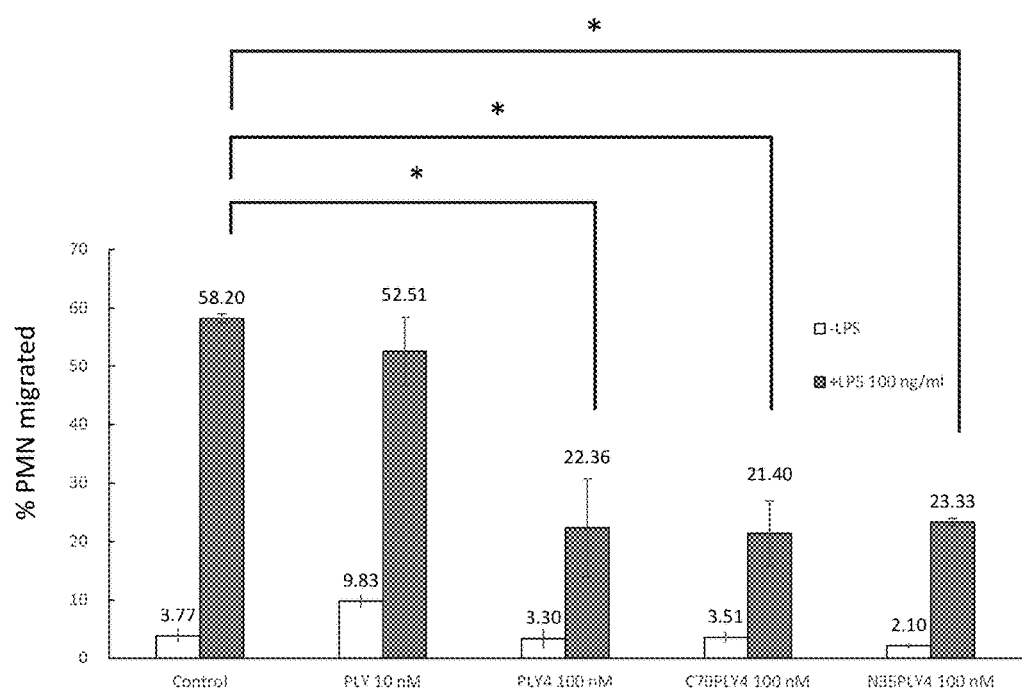
FIG. 11 shows inhibition of PMNs migration by treatment with PLY, PLY4, C70PLY4 or N35PLY4 in the wild type (WT) mice model.
Figure 12:
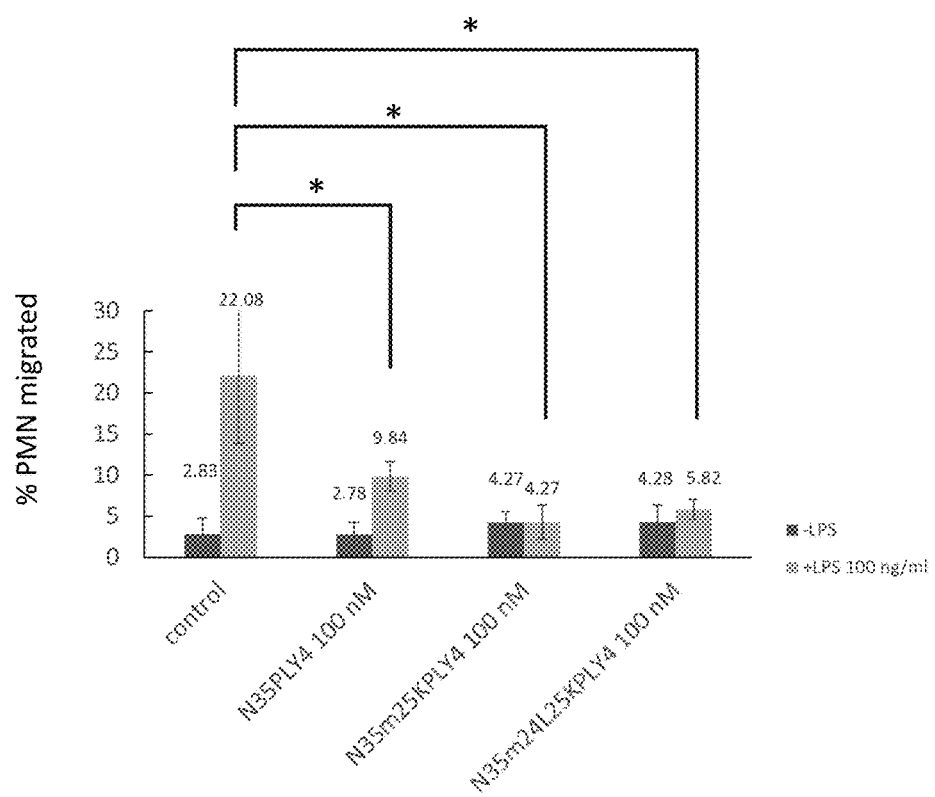
FIG. 12 shows inhibition of PMNs migration by treatment with N35PLY4, N35PLY4m25K, or N35PLY4m24L25K.

Various PLY peptides of the present disclosure were further investigated for their atherosclerosis activities. FIGS. 11-12 show that full-length PLY enhances PMN migration induced by LPS; in contrast, PLY4, C70PLY4, N35PLY4, and mutated peptides (N35PLY4m25K and N35PLY4m24L25K) have inhibitory effects in LPS induced PMN migration, which can inhibit PMN infiltration into vessel walls. Functional variants of the 35 amino acid fragments with silent mutations (e.g. (N35PLY4m25K and N35PLY4m24L25K) also have the anti-atherosclerosis activities. The results show that the N35PLY4 (SEQ ID NO: 5) is sufficient to function as a TLR4 antagonist and exhibit the anti-atherosclerosis activities of inhibition of TLR-4 ligand induced PMNs cell migration.

2.7 N-Terminal Motif "QDLTA" of the PLY Peptides of the Invention is Critical for the Function as TLR4 Antagonist MD2 is an extracellular protein that is associated with the extracellular domain of TLR4 protein. It has been demonstrated that MD2 protein is indispensable for the interaction of LPS and TLR4 protein. Kobayashi et al., J. Immunol. 176:6211-6218 (2006). Thus, in order to determine the role of C70PLY4 in TLR4 protein-elicited function, the present study examined the binding capability between C70PLY4, MD2, and TLR4 protein by the in vitro binding assay and competition binding assay. The TLR4 protein (2 μg/mL) was coated on a 96-well plate and the MD2 protein was added into the wells at various concentrations (2-fold serial dilution from 133.3 to 0.065 nM). It showed that the MD2 protein has high binding affinity to the TLR4 protein with a $K_d$ value is 18.4±3.9 nM (Kd value is a dissociation constant and it means the concentration of the ligand at which half of the proteins have bound the ligand) (FIG. 13, panel A). In the competition binding assay, we determined the blocking capability of C70PLY4, N35PLY4, or M50PLY4 peptide for the interaction of MD2 and TLR4 protein. N35PLY4 and M50PLY4 peptides were derived from the $1^{st}$ to $35^{th}$ amino acid and the $6^{th}$ to $55^{th}$ amino acid, respectively, of the C70PLY4 peptide; namely, M50PLY4 covered all amino acid of N35PLY4 except the first 5 amino acid (QDLTA, SEQ ID NO: 9). Before adding into the TLR4 protein (2 μg/mL)-coated well, the MD2 protein (50 nM) was mixed with various concentrations (2-fold serial dilution from 50 μM to 3.05 nM) of C70PLY4, N35PLY4, or M50PLY4 peptide. It was shown a dose-dependent blocking capability of C70PLY4 in the interaction between MD2 and TLR4 protein with $K_i$ of 74.8 nM (FIG. 13, panel B). The N35PLY4 showed a partial blocking capability for MD2 and TLR4 protein interaction with $K_i$ of 11224.0 nM. However, the M50PLY4 showed no competitive capability. Moreover, MD2 protein could be completely competed away by 6.25 μM of C70PLY4 and by 50 μM of N35PLY4. Thus, it has suggested that the regulatory role of C70PLY4 in TLR4-elicited function is through competing the binding site of MD2 protein in TLR4 protein. In addition, the competitive result from N35PLY4 and M50PLY4 peptides indicated that the $1^{st}$ to $5^{th}$ amino acids (QDLTA) of C70PLY4 play a critical role in the interaction of C70PLY4 and TLR4. Without amino acid of QDLTA at the C70PLY4 will lose the function to interact with TLR4.

2.8 The TLR4 Antagonistic Activity of the PLY Peptides of the Invention involves ERK1/2 and NFκB-p65 Signaling Pathway.

The present study determined if C70PLY4 inhibits LPS-induced signaling, including protein ERK1/2 and NFκB-p65 subunit, in the human umbilical vein endothelial cells (HUVECs) by using western blot assay (FIG. 14, panel A). The cells were kept as control, treated with LPS (1 μg/mL) only for 24 h, or co-treated with LPS (1 μg/mL) and C70PLY4 (100, 300, and 500 nM) for 24 h and the protein phosphorylation of ERK1/2 and NFκB-p65 subunit were examined. It was showed that LPS induces protein phosphorylation of both ERK1/2 and NFκB-p65 subunit in the HUVECs (FIG. 14, panel A). However, co-treating cells with C70PLY4 and LPS significantly inhibited the LPS effect on the ERK1/2 and NFκB-p65 subunit phosphorylation in a dose-dependent manner (FIG. 14, panel B). These results have further demonstrated that the PLY peptides of the present invention function as an potential antagonist for LPS/TLR4 signaling and act through ERK1/2 and NFκB-p65 signaling pathway.

2.9 Cytotoxicity

Figure 15:
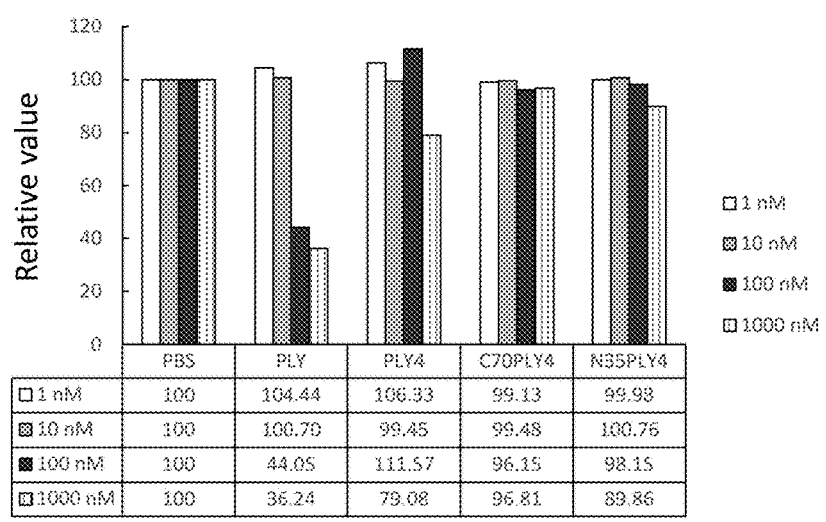
FIG. 15 shows that full-length PLY is toxic to cells and high concentration of PLY4 is slightly toxic to cells. No toxicity to cells is found by treating with C70PLY4 and N35PLY4.

The toxicity of each peptide to HUVECs was examined by using MTS assay (FIG. 15). The results shows that pneumolysin (full length) is toxic to cells at concentration of 100 nM, only 30% of cells survived; PLY4 shows slightly toxic when high concentration of PLY4; in contrast, C70PLY4 and N35PLY4 have no toxic effects to HUVECs at the same concentration (FIG. 15). The concentration (100 nM) used in following tests was based on the result of MTS assay, which is safe to cells.

Figure 16:
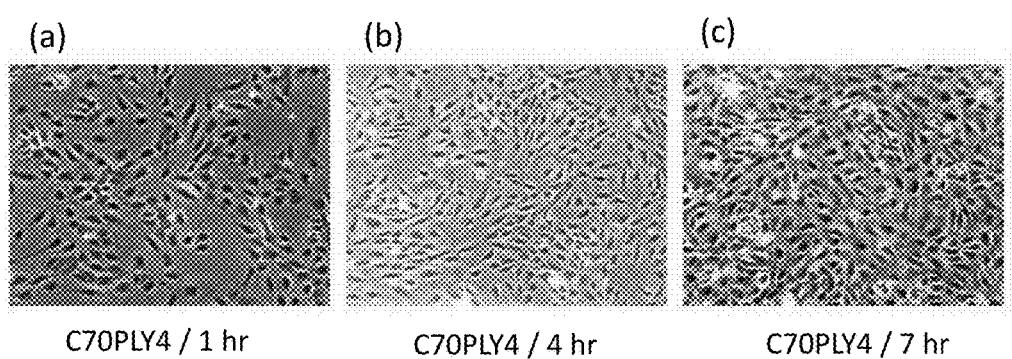
FIG. 16 shows that C70PLY4 do not affect the cell morphology of HUVEC, (a) cells treated with C70PLY4 for 1 hour, (b) cells treated with C70PLY4 for 4 hours, and (c) cells treated with C70PLY4 for 7 hours.
Figure 17:
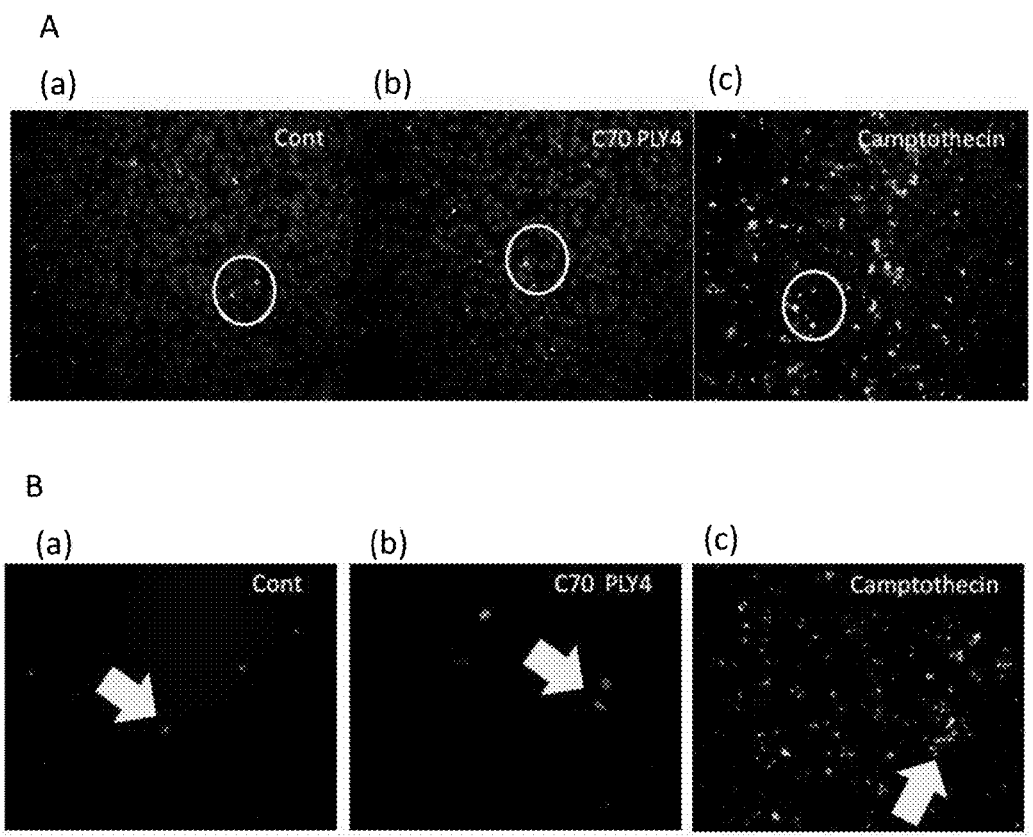
FIG. 17 includes photos showing that C70PLY4 has no apoptotic potential in the TUNEL assay (panel (A)) and that C70PLY4 has no apoptotic potential in the caspase-3 activity assay (panel (B)). (a) control cells, (b) cells treated with C70PLY4, and (c) cells treated with camptothecin (a known cytotoxic plant alkaloid).

Microscopic analysis showed C70PLY4 did not affect the cell morphology of HUVEC (FIG. 16). The MTS assays also show that C70PLY4 and PLY4 have no toxic effects to HUVECs at 100 nM or below (as described in above Results 2.9, data not shown). In addition, cell apoptosis was detected by using TUNEL and caspase-3 activity assay. The results show that C70PLY4 has no apoptotic potential, the apoptotic patterns of which have no differences in TUNEL assay (FIG. 17, panel A) and caspase-3 activity assay (FIG. 17, panel B) compared to control cells while the positive control (treated with camptothecin, a known cytotoxic plant alkaloid) has about 60% apoptotic cells.

Other Embodiments

All of the features disclosed in this specification may be combined in any combination. Each feature disclosed in this specification may be replaced by an alternative feature serving the same, equivalent, or similar purpose. Thus, unless expressly stated otherwise, each feature disclosed is only an example of a generic series of equivalent or similar features.

From the above description, one skilled in the art can easily ascertain the essential characteristics of the present invention, and without departing from the spirit and scope thereof, can make various changes and modifications of the invention to adapt it to various usages and conditions. Thus, other embodiments are also within the claims.

What is claimed is:

1. A method for inhibiting the activity of toll-like receptor 4 (TLR-4) in a subject, comprising administering to a subject in need thereof an effective amount of a pneumolysin (PLY) peptide comprising (i) a first segment that comprises the amino acid sequence QDLTA (SEQ ID NO: 9); and (ii) a second segment that comprises an amino acid sequence that is at least 90% identical to SEQ ID NO: 10; wherein the C-terminus of the first segment is linked to the N-terminus of the second segment; and wherein the PLY peptide is up to 150 amino acids in length.

2. The method of claim 1, wherein the PLY peptide blocks the binding of a MD2 protein to TLR-4.

3. The method of claim 1, wherein the subject is a human patient having or suspected of having a disease or condition associated with TLR-4 activation.

4. The method of claim 3, wherein the disease or condition associated with TLR-4 activation is an inflammatory disorder due to TLR4 activation.

5. The method of claim 4, wherein the subject is diabetic.

6. The method of claim 4, wherein the subject is a human patient having or suspected of having diabetes or a complication thereof.

7. The method of claim 6, wherein the diabetes is type II diabetes.

8. The method of claim 4, wherein the inflammatory disorder due to TLR4 activation is atherosclerosis.

9. The method of claim 1, wherein the effective amount of the PLY peptide is sufficient to lower blood glucose levels or increase insulin levels of the subject.

10. The method of claim 1, wherein the second segment in the PLY peptide comprises an amino acid sequence that is at least 97% identical to SEQ ID NO: 10.

11. The method of claim 1, wherein the second segment in the PLY peptide comprises an amino acid sequence that is at least 95% identical to SEQ ID NO: 10.

12. The method of claim 1, wherein the second segment in the PLY peptide includes mutations at up to 2 amino acid residues in SEQ ID NO: 10.

13. The method of claim 12, wherein the second segment in the PLY peptide includes one or two amino acid substitutions at one or both of positions 19 and 20 in SEQ ID NO: 10.

14. The method of claim 1, wherein the first segment in the PLY peptide is set forth as SEQ ID NO: 11.

15. The method of claim 1, wherein the first segment in the PLY peptide is set forth as SEQ ID NO: 9.

16. The method of claim 1, wherein the second segment in the PLY peptide is set forth as SEQ ID NO: 10, 12, 13 or 14.

17. The method of claim 1, wherein the PLY peptide comprises an amino acid sequence selected from the group consisting of SEQ ID NOs: 3-7.

18. The method of claim 1, wherein the second segment in the PLY peptide has a substitution of amino acid residue at I19, R20, or both in SEQ ID NO: 10.

19. The method of claim 18, wherein the substitution of amino acid residue comprises I19L, R20K, or a combination thereof.

* * * * *

SEQUENCE LISTING

<160> NUMBER OF SEQ ID NOS: 17

<210> SEQ ID NO 1
<211> LENGTH: 471
<212> TYPE: PRT
<213> ORGANISM: Streptococcus pneumoniae

<400> SEQUENCE: 1

Met Ala Asn Lys Ala Val Asn Asp Phe Ile Leu Ala Met Asn Tyr Asp

-continued

```
1               5                   10                  15
Lys Lys Lys Leu Leu Thr His Gln Gly Glu Ser Ile Glu Asn Arg Phe
            20                  25                  30

Ile Lys Glu Gly Asn Gln Leu Pro Asp Glu Phe Val Val Ile Glu Arg
            35                  40                  45

Lys Lys Arg Ser Leu Ser Thr Asn Thr Ser Asp Ile Ser Val Thr Ala
50                  55                  60

Thr Asn Asp Ser Arg Leu Tyr Pro Gly Ala Leu Leu Val Val Asp Glu
65                  70                  75                  80

Thr Leu Leu Glu Asn Asn Pro Thr Leu Leu Ala Val Asp Arg Ala Pro
                85                  90                  95

Met Thr Tyr Ser Ile Asp Leu Pro Gly Leu Ala Ser Ser Asp Ser Phe
                100                 105                 110

Leu Gln Val Glu Asp Pro Ser Asn Ser Ser Val Arg Gly Ala Val Asn
            115                 120                 125

Asp Leu Leu Ala Lys Trp His Gln Asp Tyr Gly Gln Val Asn Asn Val
            130                 135                 140

Pro Ala Arg Met Gln Tyr Glu Lys Ile Thr Ala His Ser Met Glu Gln
145                 150                 155                 160

Leu Lys Val Lys Phe Gly Ser Asp Phe Glu Lys Thr Gly Asn Ser Leu
                165                 170                 175

Asp Ile Asp Phe Asn Ser Val His Ser Gly Glu Lys Gln Ile Gln Ile
            180                 185                 190

Val Asn Phe Lys Gln Ile Tyr Tyr Thr Val Ser Val Asp Ala Val Lys
            195                 200                 205

Asn Pro Gly Asp Val Phe Gln Asp Thr Val Thr Val Glu Asp Leu Lys
210                 215                 220

Gln Arg Gly Ile Ser Ala Glu Arg Pro Leu Val Tyr Ile Ser Ser Val
225                 230                 235                 240

Ala Tyr Gly Arg Gln Val Tyr Leu Lys Leu Glu Thr Thr Ser Lys Ser
                245                 250                 255

Asp Glu Val Glu Ala Ala Phe Glu Ala Leu Ile Lys Gly Val Lys Val
            260                 265                 270

Ala Pro Gln Thr Glu Trp Lys Gln Ile Leu Asp Asn Thr Glu Val Lys
            275                 280                 285

Ala Val Ile Leu Gly Gly Asp Pro Ser Ser Gly Ala Arg Val Val Thr
            290                 295                 300

Gly Lys Val Asp Met Val Glu Asp Leu Ile Gln Glu Gly Ser Arg Phe
305                 310                 315                 320

Thr Ala Asp His Pro Gly Leu Pro Ile Ser Tyr Thr Thr Ser Phe Leu
                325                 330                 335

Arg Asp Asn Val Val Ala Thr Phe Gln Asn Ser Thr Asp Tyr Val Glu
            340                 345                 350

Thr Lys Val Thr Ala Tyr Arg Asn Gly Asp Leu Leu Leu Asp His Ser
            355                 360                 365

Gly Ala Tyr Val Ala Gln Tyr Tyr Ile Thr Trp Asn Glu Leu Ser Tyr
            370                 375                 380

Asp His Gln Gly Lys Glu Val Leu Thr Pro Lys Ala Trp Asp Arg Asn
385                 390                 395                 400

Gly Gln Asp Leu Thr Ala His Phe Thr Thr Ser Ile Pro Leu Lys Gly
                405                 410                 415

Asn Val Arg Asn Leu Ser Val Lys Ile Arg Glu Cys Thr Gly Leu Ala
            420                 425                 430
```

```
Trp Glu Trp Trp Arg Thr Val Tyr Glu Lys Thr Asp Leu Pro Leu Val
        435                 440                 445

Arg Lys Arg Thr Ile Ser Ile Trp Gly Thr Thr Leu Tyr Pro Gln Val
450                 455                 460

Glu Asp Lys Val Glu Asn Asp
465                 470

<210> SEQ ID NO 2
<211> LENGTH: 359
<212> TYPE: PRT
<213> ORGANISM: Artificial Sequence
<220> FEATURE:
<223> OTHER INFORMATION: Synthetic Polypeptide

<400> SEQUENCE: 2

Met Ala Asn Lys Ala Val Asn Asp Phe Ile Leu Ala Met Asn Tyr Asp
1               5                   10                  15

Lys Lys Lys Leu Leu Thr His Gln Gly Glu Ser Ile Glu Asn Arg Phe
            20                  25                  30

Ile Lys Glu Gly Asn Gln Leu Pro Asp Glu Phe Val Val Ile Glu Arg
        35                  40                  45

Lys Lys Arg Ser Leu Ser Thr Asn Thr Ser Asp Ile Ser Val Thr Ala
50                  55                  60

Thr Asn Asp Ser Arg Leu Tyr Pro Gly Ala Leu Leu Val Val Asp Glu
65                  70                  75                  80

Thr Leu Leu Glu Asn Asn Pro Thr Leu Leu Ala Val Asp Arg Ala Pro
                85                  90                  95

Met Thr Tyr Ser Ile Asp Leu Pro Gly Leu Ala Ser Ser Asp Ser Phe
            100                 105                 110

Leu Gln Val Glu Asp Pro Ser Asn Ser Ser Val Arg Gly Ala Val Asn
        115                 120                 125

Asp Leu Leu Ala Lys Trp His Gln Asp Tyr Gly Gln Val Asn Asn Val
130                 135                 140

Pro Ala Arg Met Gln Tyr Glu Lys Ile Thr Ala His Ser Met Glu Gln
145                 150                 155                 160

Leu Lys Val Lys Phe Gly Ser Asp Phe Glu Lys Thr Gly Asn Ser Leu
                165                 170                 175

Asp Ile Asp Phe Asn Ser Val His Ser Gly Glu Lys Gln Ile Gln Ile
            180                 185                 190

Val Asn Phe Lys Gln Ile Tyr Tyr Thr Val Ser Val Asp Ala Val Lys
        195                 200                 205

Asn Pro Gly Asp Val Phe Gln Asp Thr Val Thr Val Glu Asp Leu Lys
210                 215                 220

Gln Arg Gly Ile Ser Ala Glu Arg Pro Leu Val Tyr Ile Ser Ser Val
225                 230                 235                 240

Ala Tyr Gly Arg Gln Val Tyr Leu Lys Leu Glu Thr Thr Ser Lys Ser
                245                 250                 255

Asp Glu Val Glu Ala Ala Phe Glu Ala Leu Ile Lys Gly Val Lys Val
            260                 265                 270

Ala Pro Gln Thr Glu Trp Lys Gln Ile Leu Asp Asn Thr Glu Val Lys
        275                 280                 285

Ala Val Ile Leu Gly Gly Asp Pro Ser Ser Gly Ala Arg Val Val Thr
290                 295                 300

Gly Lys Val Asp Met Val Glu Asp Leu Ile Gln Glu Gly Ser Arg Phe
305                 310                 315                 320
```

```
Thr Ala Asp His Pro Gly Leu Pro Ile Ser Tyr Thr Ser Phe Leu
                325                 330                 335

Arg Asp Asn Val Val Ala Thr Phe Gln Asn Ser Thr Asp Tyr Val Glu
            340                 345                 350

Thr Lys Val Thr Ala Tyr Arg
        355

<210> SEQ ID NO 3
<211> LENGTH: 112
<212> TYPE: PRT
<213> ORGANISM: Artificial Sequence
<220> FEATURE:
<223> OTHER INFORMATION: Synthetic Polypeptide

<400> SEQUENCE: 3

Asn Gly Asp Leu Leu Asp His Ser Gly Ala Tyr Val Ala Gln Tyr
1               5                   10                  15

Tyr Ile Thr Trp Asn Glu Leu Ser Tyr Asp His Gln Gly Lys Glu Val
            20                  25                  30

Leu Thr Pro Lys Ala Trp Asp Arg Asn Gly Gln Asp Leu Thr Ala His
            35                  40                  45

Phe Thr Thr Ser Ile Pro Leu Lys Gly Asn Val Arg Asn Leu Ser Val
50                  55                  60

Lys Ile Arg Glu Cys Thr Gly Leu Ala Trp Glu Trp Trp Arg Thr Val
65                  70                  75                  80

Tyr Glu Lys Thr Asp Leu Pro Leu Val Arg Lys Arg Thr Ile Ser Ile
                85                  90                  95

Trp Gly Thr Thr Leu Tyr Pro Gln Val Glu Asp Lys Val Glu Asn Asp
            100                 105                 110

<210> SEQ ID NO 4
<211> LENGTH: 70
<212> TYPE: PRT
<213> ORGANISM: Artificial Sequence
<220> FEATURE:
<223> OTHER INFORMATION: Synthetic Polypeptide

<400> SEQUENCE: 4

Gln Asp Leu Thr Ala His Phe Thr Thr Ser Ile Pro Leu Lys Gly Asn
1               5                   10                  15

Val Arg Asn Leu Ser Val Lys Ile Arg Glu Cys Thr Gly Leu Ala Trp
            20                  25                  30

Glu Trp Trp Arg Thr Val Tyr Glu Lys Thr Asp Leu Pro Leu Val Arg
            35                  40                  45

Lys Arg Thr Ile Ser Ile Trp Gly Thr Thr Leu Tyr Pro Gln Val Glu
        50                  55                  60

Asp Lys Val Glu Asn Asp
65                  70

<210> SEQ ID NO 5
<211> LENGTH: 35
<212> TYPE: PRT
<213> ORGANISM: Artificial Sequence
<220> FEATURE:
<223> OTHER INFORMATION: Synthetic Polypeptide

<400> SEQUENCE: 5

Gln Asp Leu Thr Ala His Phe Thr Thr Ser Ile Pro Leu Lys Gly Asn
1               5                   10                  15
```

```
Val Arg Asn Leu Ser Val Lys Ile Arg Glu Cys Thr Gly Leu Ala Trp
            20                  25                  30

Glu Trp Trp
        35

<210> SEQ ID NO 6
<211> LENGTH: 35
<212> TYPE: PRT
<213> ORGANISM: Artificial Sequence
<220> FEATURE:
<223> OTHER INFORMATION: Synthetic Polypeptide

<400> SEQUENCE: 6

Gln Asp Leu Thr Ala His Phe Thr Thr Ser Ile Pro Leu Lys Gly Asn
1               5                   10                  15

Val Arg Asn Leu Ser Val Lys Ile Lys Glu Cys Thr Gly Leu Ala Trp
            20                  25                  30

Glu Trp Trp
        35

<210> SEQ ID NO 7
<211> LENGTH: 35
<212> TYPE: PRT
<213> ORGANISM: Artificial Sequence
<220> FEATURE:
<223> OTHER INFORMATION: Synthetic Polypeptide

<400> SEQUENCE: 7

Gln Asp Leu Thr Ala His Phe Thr Thr Ser Ile Pro Leu Lys Gly Asn
1               5                   10                  15

Val Arg Asn Leu Ser Val Lys Leu Lys Glu Cys Thr Gly Leu Ala Trp
            20                  25                  30

Glu Trp Trp
        35

<210> SEQ ID NO 8
<211> LENGTH: 50
<212> TYPE: PRT
<213> ORGANISM: Artificial Sequence
<220> FEATURE:
<223> OTHER INFORMATION: Synthetic Polypeptide

<400> SEQUENCE: 8

His Phe Thr Thr Ser Ile Pro Leu Lys Gly Asn Val Arg Asn Leu Ser
1               5                   10                  15

Val Lys Ile Arg Glu Cys Thr Gly Leu Ala Trp Glu Trp Trp Arg Thr
            20                  25                  30

Val Tyr Glu Lys Thr Asp Leu Pro Leu Val Arg Lys Arg Thr Ile Ser
        35                  40                  45

Ile Trp
    50

<210> SEQ ID NO 9
<211> LENGTH: 5
<212> TYPE: PRT
<213> ORGANISM: Artificial Sequence
<220> FEATURE:
<223> OTHER INFORMATION: Synthetic Polypeptide

<400> SEQUENCE: 9

Gln Asp Leu Thr Ala
1               5
```

<210> SEQ ID NO 10
<211> LENGTH: 30
<212> TYPE: PRT
<213> ORGANISM: Artificial Sequence
<220> FEATURE:
<223> OTHER INFORMATION: Synthetic Polypeptide

<400> SEQUENCE: 10

His Phe Thr Thr Ser Ile Pro Leu Lys Gly Asn Val Arg Asn Leu Ser
1               5                   10                  15

Val Lys Ile Arg Glu Cys Thr Gly Leu Ala Trp Glu Trp Trp
            20                  25                  30

<210> SEQ ID NO 11
<211> LENGTH: 47
<212> TYPE: PRT
<213> ORGANISM: Artificial Sequence
<220> FEATURE:
<223> OTHER INFORMATION: Synthetic Polypeptide

<400> SEQUENCE: 11

Asn Gly Asp Leu Leu Asp His Ser Gly Ala Tyr Val Ala Gln Tyr
1               5                   10                  15

Tyr Ile Thr Trp Asn Glu Leu Ser Tyr Asp His Gln Gly Lys Glu Val
            20                  25                  30

Leu Thr Pro Lys Ala Trp Asp Arg Asn Gly Gln Asp Leu Thr Ala
        35                  40                  45

<210> SEQ ID NO 12
<211> LENGTH: 65
<212> TYPE: PRT
<213> ORGANISM: Artificial Sequence
<220> FEATURE:
<223> OTHER INFORMATION: Synthetic Polypeptide

<400> SEQUENCE: 12

His Phe Thr Thr Ser Ile Pro Leu Lys Gly Asn Val Arg Asn Leu Ser
1               5                   10                  15

Val Lys Ile Arg Glu Cys Thr Gly Leu Ala Trp Glu Trp Trp Arg Thr
            20                  25                  30

Val Tyr Glu Lys Thr Asp Leu Pro Leu Val Arg Lys Arg Thr Ile Ser
        35                  40                  45

Ile Trp Gly Thr Thr Leu Tyr Pro Gln Val Glu Asp Lys Val Glu Asn
    50                  55                  60

Asp
65

<210> SEQ ID NO 13
<211> LENGTH: 30
<212> TYPE: PRT
<213> ORGANISM: Artificial Sequence
<220> FEATURE:
<223> OTHER INFORMATION: Synthetic Polypeptide

<400> SEQUENCE: 13

His Phe Thr Thr Ser Ile Pro Leu Lys Gly Asn Val Arg Asn Leu Ser
1               5                   10                  15

Val Lys Ile Lys Glu Cys Thr Gly Leu Ala Trp Glu Trp Trp
            20                  25                  30

<210> SEQ ID NO 14
<211> LENGTH: 30

-continued

```
<212> TYPE: PRT
<213> ORGANISM: Artificial Sequence
<220> FEATURE:
<223> OTHER INFORMATION: Synthetic Polypeptide

<400> SEQUENCE: 14

His Phe Thr Thr Ser Ile Pro Leu Lys Gly Asn Val Arg Asn Leu Ser
1               5                   10                  15

Val Lys Leu Lys Glu Cys Thr Gly Leu Ala Trp Glu Trp Trp
            20                  25                  30

<210> SEQ ID NO 15
<211> LENGTH: 31
<212> TYPE: DNA
<213> ORGANISM: Artificial Sequence
<220> FEATURE:
<223> OTHER INFORMATION: Synthetic Polynucleotide

<400> SEQUENCE: 15
ggaattccat atgaacggag atttactgct g                                     31

<210> SEQ ID NO 16
<211> LENGTH: 33
<212> TYPE: DNA
<213> ORGANISM: Artificial Sequence
<220> FEATURE:
<223> OTHER INFORMATION: Synthetic Polynucleotide

<400> SEQUENCE: 16
ccgctcgagg tcattttcta ccttatcttc tac                                   33

<210> SEQ ID NO 17
<211> LENGTH: 8
<212> TYPE: PRT
<213> ORGANISM: Artificial Sequence
<220> FEATURE:
<223> OTHER INFORMATION: Synthetic Polypeptide

<400> SEQUENCE: 17

Leu Glu His His His His His His
1               5
```